United States Patent [19]

Berger et al.

[11] Patent Number: 4,520,193
[45] Date of Patent: * May 28, 1985

[54] CEPHALOSPORIN DERIVATIVES

[75] Inventors: Christian Berger, Le Plessis Robinson; Daniel Farge, Thiais; Claude Moutonnier, Le Plessis Robinson; Gerard Wolff, Thiais, all of France

[73] Assignee: Rhone-Poulenc Industries, Paris, France

[*] Notice: The portion of the term of this patent subsequent to Dec. 22, 1998 has been disclaimed.

[21] Appl. No.: 322,961

[22] Filed: Nov. 19, 1981

[30] Foreign Application Priority Data

Nov. 20, 1980 [FR] France ................................ 80 24638

[51] Int. Cl.$^3$ .................. C07D 501/38; A61K 31/545
[52] U.S. Cl. ...................... 544/016; 544/26; 544/27; 544/22; 544/21; 544/25
[58] Field of Search ............... 544/16, 22; 542/420, 542/419; 424/246

[56] References Cited

U.S. PATENT DOCUMENTS 4,278,793 7/1981 Dürchheimer et al. ............. 544/23
4,307,233 12/1981 Farge et al. ........................ 542/420

Primary Examiner—Nicholas S. Rizzo
Attorney, Agent, or Firm—Stevens, Davis, Miller & Mosher

[57] ABSTRACT

The invention provides new cephalosporin derivatives of the general formula,

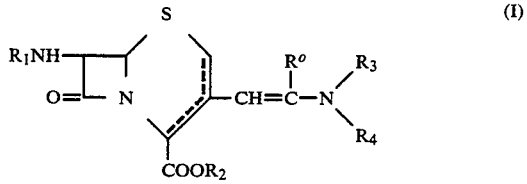

which are in the form of a bicyclooct-2-ene or bicyclooct-3-ene, in which formula $R_1$ is a radical of the general formula

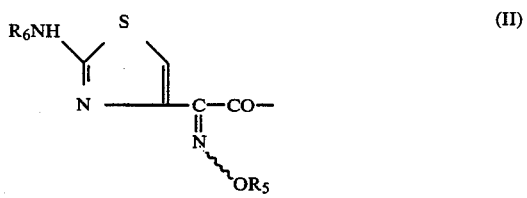

[in which $R_5$ is hydrogen, alkyl, vinyl, cyanomethyl, protected carboxyalkyl or a protective radical and $R_6$ is a protective radical] or an amino-protecting radical, $R_2$ is an acid-protecting radical and $R°$ represents various organic radicals, or alternatively $R_1$ is an amino-protecting radical or various acyl radicals, $R_2$ is a protective radical and $R°$ represents various organic radicals, and $R_3$ and $R_4$ are alkyl radicals optionally substituted by alkoxy or dialkylamino, or phenyl radicals, or —$NR_3R_4$ forms a heterocyclic ring. These products are intermediates for the synthesis of cephalosporins having antibacterial activity.

13 Claims, No Drawings

CEPHALOSPORIN DERIVATIVES

The present invention relates to new 3-vinylcephalosporin derivatives of the general formula:

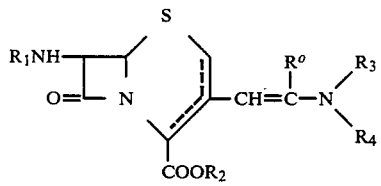

and their preparation.

The product of the general formula (I) is in the form of a bicyclooct-2-ene or bicyclooct-3-ene (according to the nomenclature of Chemical Abstracts), the substituents $R°$ and $-NR_3R_4$ of the chain in the 3-position can be in the cis or trans position of the bicyclooctene, and the symbols $R_3$ and $R_4$, which are identical or different, represent alkyl radicals (optionally substituted by an alkoxy or dialkylamino radical) or phenyl radicals, or together form, with the nitrogen atom to which they are attached, a 5- or 6-membered saturated heterocyclic ring optionally containing another hetero-atom chosen from amongst nitrogen, oxygen or sulphur, and optionally substituted by an alkyl radical, and (a) the symbol $R_1$ represents a radical of the general formula:

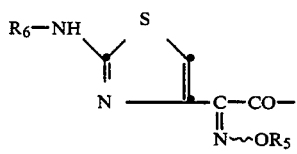

[[in which $R_5$ is a hydrogen atom, an alkyl, vinyl or cyanomethyl radical, an oxime-protecting group such as trityl, tetrahydropyranyl or 2-methoxyprop-2-yl, or a radical of the general formula:

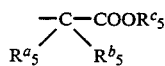

(in which $R^a{}_5$ and $R^b{}_5$, which are identical or different, are hydrogen atoms or alkyl radicals or together form an alkylene radical containing 2 or 3 carbon atoms, and $R^c{}_5$ is an acid-protecting radical, e.g. such as mentioned below for $R_2$) and $R_6$ is an amine-protecting radical such as t-butoxycarbonyl, trityl, benzyl, dibenzyl, benzyloxycarbonyl, p-nitrobenzyloxycarbonyl or p-methoxybenzyloxycarbonyl, or the radical of the general formula (V) defined below]], a benzhydryl or trityl radical, an acyl radical of the general formula:

   $R_7-CO-$   (III)

[[in which $R_7$ is an alkyl radical (substituted by a phenyl or phenoxy radical)]], a radical of the general formula:

   $R_8OCO-$   (IV)

[[in which $R_8$ is an unsubstituted branched alkyl radical or a branched or linear alkyl radical carrying 1 or more substituents [chosen from amongst phenyl and phenyl substituted by an alkoxy, nitro or phenyl radical] or a vinyl radical]], or a radical of the general formula:

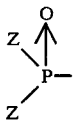

(in which the symbols Z represent phenyl radicals or radicals OZ', in which the symbols Z' represent alkyl, 2,2,2-trichloroethyl, phenyl or benzyl radicals, it being possible for these last 2 radicals to be substituted by a halogen atom or an alkyl, alkoxy or nitro radical, or alternatively the symbols Z' of the 2 substituents Z together form an alkylene radical containing 2 or 3 carbon atoms), or alternatively $R_1NH$ is replaced by a methyleneamino radical in which the methylene radical is substituted by a dialkylamino or aryl group (which is itself optionally substituted by one or more methoxy or nitro radicals), the symbol $R_2$ represents an acid-protecting radical such as methoxymethyl, t-butyl, benzhydryl, benzyl, nitrobenzyl or p-methoxybenzyl, and the symbol $R°$ is a radical of a first group consisting of a phenyl radical optionally substituted by an alkyl, trifluoromethyl, dialkylaminomethyl, alkoxy, alkylthio or dialkylamino radical or by a halogen atom such as fluorine or chlorine, or a 5- or 6-membered heterocyclic radical containing a single hetero-atom (such as pyrid-2-yl or pyrid-3-yl, thien-2-yl or thien-3-yl or furan-2-yl or furan-3-yl), which is optionally substituted by an alkyl, alkoxy or dimethylaminomethyl radical, or a radical of a second group (which will hereafter be designated as a "radical $-CHR_9R_{10}$") consisting of an alkyl radical containing 1 to 5 carbon atoms, a benzyl radical optionally substituted by a halogen atom or an alkyl, alkoxy, alkylthio, dialkylamino or trifluoromethyl radical, a methyl radical substituted by a 5- or 6-membered aromatic heterocyclic ring such as pyrid-2-yl or pyrid-3-yl, thien-2-yl or thien-3-yl or furan-2-yl or furan-3-yl, a cycloalkyl radical containing 3 to 6 ring members, or a radical in which $R_9$ and $R_{10}$, together with the carbon atom to which they are attached, form a 5- or 6-membered heterocyclic radical containing an oxygen or sulphur atom or alternatively (b) the symbol $R_1$ represents an amino-protecting radical such as trityl or silyl, an alkoxycarbonyl radical, the alkyl part of which contains 1 to 5 carbon atoms, and which is preferably branched on the carbon atom in the α-position to the oxygen atom (and/or optionally substituted by one or more phenyl or furyl radicals, e.g. α-phenylalkoxycarbonyl, diphenylmethoxycarbonyl or α-furylalkoxycarbonyl), a 2-(biphenyl-4-yl)-propoxycarbonyl radical, or a radical of the general formula:

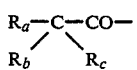

in which $R_a$ is an optionally substituted phenyl, thienyl, furyl, cyclohexadienyl or cyclohexenyl radical, $R_b$ is a hydrogen atom and $R_c$ is a hydrogen atom, an optionally protected hydroxyl radical, a protected amino radical or an optionally protected sulpho radical, or $R_a$ is an optionally substituted phenoxy radical or a pyridylthio radical and $R_b$ and $R_c$ are hydrogen atoms, or alternatively $R_a$ is a phenyl, thienyl or furyl radical and $R_b$ and $R_c$ together form an alkoxyimino, cycloalkoxyimino or phenylalkoxyimino radical in the syn form.

The phenyl and phenoxy radicals can be substituted by hydroxyl, alkoxy, acyloxy, benzoyloxy, 4-carbamoyloxy groups, protected amino or alkylamino groups or dialkylamino, alkylsulphonylamino, aminomethyl or t-butoxycarbonylaminomethyl groups or by a halogen atom.

The thienyl, furyl, cyclohexadienyl and cyclohexenyl radicals can be substituted by protected aminomethyl radicals, in particular in the 5-position on the thienyl and furyl radicals and in the 2- or 3-position on the cyclohexadienyl and cyclohexenyl radicals.

The hydroxyl, amino and sulpho radicals represented by $R_c$ can be protected by any known group, the introduction and removal of which do not affect the rest of the molecule. The hydroxyl-protecting groups are in particular those mentioned in French patent application No. 2,321,294, except for the halogen-containing groups or the stannyl group.

The symbol $R_2$ represents a protective radical such as an aryl group polysubstituted by aliphatic or aromatic radicals such as alkyl or phenyl, an aromatic heterocyclic group containing oxygen or sulphur, a substituted methyl group such as t-alkyl (containing 4 or 5 carbon atoms), optionally substituted diphenylmethyl (e.g. 4,4'-dimethoxydiphenylmethyl), alkoxyphenylalkyl (e.g. methoxybenzyl or dimethoxybenzyl), nitrobenzyl, 4,5-dimethoxy-2-nitrobenzyl or furfuryl, or a 5- to 7-membered 2-oxa (or 2-thia)-cycloalkyl or 2-oxa (or 2-thia)-cycloalkenyl group, or a nitrophenyl or 2,4-dinitrophenyl group, or also a silyl radical substituted e.g. by alkoxy, cycloalkyl, phenyl or phenylalkyl radicals, in particular trialkylsilyl, and the symbol $R°$ represents an alkyl radical (containing 1 to 7 carbon atoms), a cycloalkyl radical (containing 3 to 7 carbon atoms), a cycloalkyl-alkyl radical (containing 4 to 7 carbon atoms), a monocyclic or bicyclic aryl radical such as phenyl or naphthyl, an arylalkyl radical such as phenylalkyl, or a heterocyclic or heterocyclylalkyl radical in which the heterocyclic ring is preferably a 5- or 6-membered aromatic ring and contains 1 to 4 nitrogen atoms and/or an oxygen or sulphur atom, such as pyrrolyl, pyrid-2-yl (or pyrid-3-yl), thienyl, furyl, imidazolyl, tetrazolyl, thiazolyl or isothiazolyl, it being possible for all these radicals $R°$ to be optionally substituted by alkyl or alkoxy radicals.

It is understood that, unless otherwise mentioned, the alkyl or acyl portions or radicals which have been mentioned above or which will be mentioned below are linear or branched and contain 1 to 4 carbon atoms.

In the general formula (I), the radicals $R°$ and $-NR_3R_4$ can be respectively in the cis and trans position, or vice versa.

Hereafter, the trans stereoisomer will be designated by E and the cis stereoisomer will be designated by Z.

It is understood that mixtures of the bicyclooct-2-ene and bicyclooct-3-ene isomers and/or Z and E isomers fall within the scope of the present invention.

Furthermore, it is also understood that the group $-OR_5$ of the radical of the general formula (II) can be in either the syn or anti position and that these isomers and mixtures thereof also fall within the scope of the present invention.

The syn form can be represented by the formula

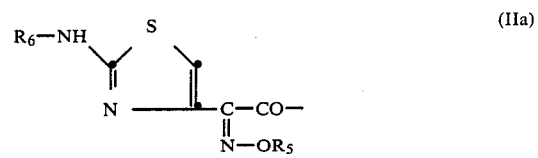

The anti form can be represented by the formula

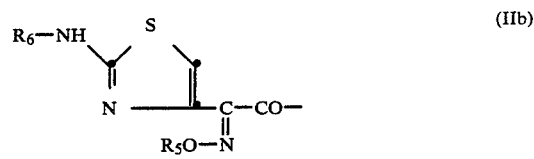

Amongst the meanings of $R_1$ defined above under (a), the following may be mentioned in particular: 2-methoxyimino-2-(2-tritylaminothiazol-4-yl)-acetyl, 2-methoxyimino-2-(2-t-butoxycarbonylaminothiazol-4-yl)-acetyl, 2-trityloxyimino-2-(2-tritylaminothiazol-4-yl)-acetyl, 2-tetrahydropyranyloxyimino-2-(2-tritylaminothiazol-4-yl)-acetyl, 2-t-butoxycarbonylmethoxyimino-2-(2-tritylaminothiazol-4-yl)-acetyl, trityl, phenylacetyl, phenoxyacetyl, t-butoxycarbonyl, benzyloxycarbonyl, p-methoxybenzyloxycarbonyl, p-nitrobenzyloxycarbonyl, diphenylmethoxycarbonyl, 2-(biphenyl-4-yl)-isopropoxycarbonyl, vinyloxycarbonyl, diphenylphosphinoyl, dimethoxyphosphoryl, diethoxyphosphoryl and diphenoxyphosphoryl.

The following may be mentioned as examples of methyleneamino radicals: dimethylaminomethyleneamino, 3,4-dimethoxybenzylideneamino and 4-nitrobenzylideneamino.

1. According to the invention, the products of the general formula (I) in which $R_1$, $R_2$, $R_3$ and $R_4$ have the definitions given above and $R°$ is a radical of the first group defined above under (a) or represents a radical defined under (b) chosen from amongst aryl or heterocyclic radicals, can be obtained by reacting a reactant, optionally prepared in situ, of the general formula:

in which $R°$, $R_3$ and $R_4$ are defined as above, with a cephalosporin derivative of the general formula:

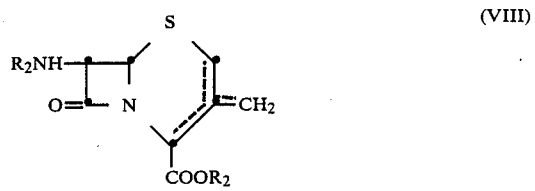

in which, $R_1$ and $R_2$ being defined as above, the derivative is in the form of a 3-methyl-bicyclooct-2-ene or -bicyclooct-3-ene or a 3-methylenebicyclooctane.

The reaction is generally carried out in an organic solvent such as dimethylformamide, hexamethylphosphorotriamide, glymes, dioxane, dimethylacetamide or ethyl acetate, or in a mixture of such solvents, at a temperature between 20° C. and the reflux temperature of the reaction mixture.

2. According to the invention, the products of the general formula (I) in which $R_1$, $R_2$, $R_3$ and $R_4$ are defined as above and R° is a radical of the second group defined above under (a) or represents a radical defined under (b), chosen from amongst alkyl, cycloalkyl, arylalkyl or heterocyclylalkyl radicals, can be obtained by reacting a reactant, optionally prepared in situ, of the general formula:

(in which $R_9$ and $R_{10}$ are such that $R_9R_{10}CH-$ represents the radical R° defined above, $R_3$ and $R_4$ are defined as above and $R_{11}$ is an alkyl radical containing 1 to 5 carbon atoms) with a cephalosporin derivative of the general formula (VIII).

The reaction is generally carried out under the conditions described above for the preparation of the products of the general formula (I) from the products (VII) and (VIII).

The reactants of the general formula (VII) can be obtained in accordance with or by application of the method described by C. F. HOBBS et al., J. Org. Chem., 36, 2,885 (1971).

The reactants of the general formula (IXa) can be obtained in accordance with or by application of the method described by H. BREDERECK et al., Chem. Ber., 97, 3,076 (1964) and Chem. Ber., 97, 3,081 (1964).

The cephalosporin derivatives of the general formula (VIII) in which $R_1$ represents a radical of the general formula (II) can be prepared from the products of the general formula:

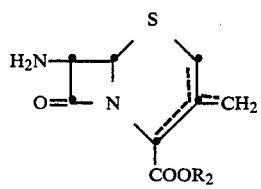

[in which, $R_2$ being defined as above, the position of the double bond is defined as for the product of the general formula (VIII)] by reaction with an acid of the general formula

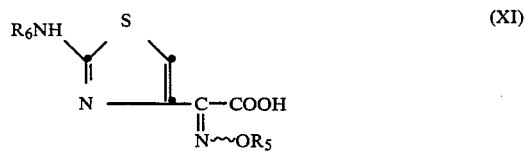

[in which $R_5$ and $R_6$ are defined as above, except that $R_5$ cannot represent the hydrogen atom] or with a reactive derivative of this acid, this being followed, if necessary, by the removal of the oxime-protecting radical. It is understood that the acid of the general formula (XI) in the syn or anti form, or mixtures thereof, leads respectively to the products of the general formula (VIII) in the syn or anti form, or to mixtures thereof.

In general, the condensation of the product of the general formula (XI), in which the acid group is free, with the 7-aminocephalosporin of the general formula (X) is carried out in an organic solvent such as dimethylformamide, acetonitrile, tetrahydrofuran, methylene chloride or chloroform, in the presence of a condensation agent such as a carbodiimide (e.g. dicyclohexylcarbodiimide), N,N-carbonyldiimidazole or 2-ethoxy-1-ethoxycarbonyl-1,2-dihydroquinoline, at a temperature between $-20°$ and $40°$ C.

If a reactive derivative of the acid of the general formula (XI) is used, it is possible to use the anhydride, a mixed anhydride or a reactive ester of the general formula

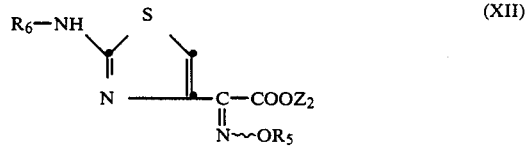

[[in which, $R_5$ and $R_6$ being defined as above, $Z_2$ represents a succinimido, benzotriazol-1-yl, 4-nitrophenyl, 2,4-dinitrophenyl, pentachlorophenyl or phthalimido radical]] or an acid halide, e.g. the acid chloride.

If the anhydride, a mixed anhydride or an acid halide (which can all be prepared in situ) is used, the condensation is carried out in an inert organic solvent such as an ether (e.g. tetrahydrofuran or dioxane), a chlorinated solvent (e.g. chloroform or methylene chloride), an amide (e.g. dimethylformamide or dimethylacetamide) or a ketone (e.g. acetone), or mixtures of these solvents [in the presence of an acid acceptor such as an epoxide (e.g. propylene oxide) or such as a nitrogen-containing organic base like pyridine, dimethylaminopyridine, N-methylmorpholine or a trialkylamine (e.g. triethylamine)], or in an aqueous-organic medium, in the presence of an alkaline condensation agent such as sodium bicarbonate, and the reaction is carried out at a temperature between $-40°$ and $+40°$ C.

If a reactive ester of the general formula (XII) is used, the reaction is generally carried out in the presence of a trialkylamine (e.g. triethylamine), in an organic solvent such as dimethylformamide, at a temperature between $0°$ and $40°$ C.

The introduction of the protective groups $R_1$ and/or $R_2$ of the products of the general formula (VIII) in which $R_1$ and $R_2$ are defined as above under (a) [except that $R_1$ cannot represent a radical of the general formula (II)], and of the products of the general formula (X) in which $R_2$ is defined as above under (a), can be carried out on a cephalosporin respectively of the general formula (X) or of the general formula:

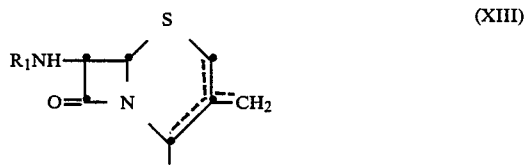

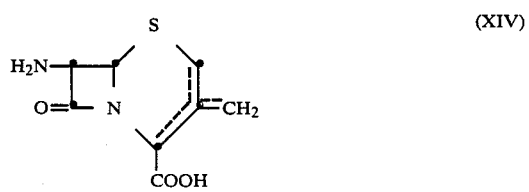

by applying the methods described in the following references:

if $R_1$ is a trityl radical: by analogy with the method described by J. C. SHEEHAN et al., J. Amer. Chem. Soc., 84, 2,983 (1962), if $R_1$ is phenylacetyl or phenoxyacetyl: according to E. H. FLYNN, Cephalosporins and Penicillins, Ac. Press (1972), if $R_1$ is a t-butoxycarbonyl radical: according to L. MORODER et al., Hoppe Seyler's Z. Physiol. Chem., 357, 1,651 (1976), if $R_1$ is benzyloxycarbonyl, p-methoxybenzyloxycarbonyl, p-nitrobenzyloxycarbonyl or vinyloxycarbonyl: by reaction with a chloroformate in an aqueous-organic medium, in the presence of an alkali metal bicarbonate, or according to Belgian Pat. No. 788,885, if $R_1$ is diphenylmethoxycarbonyl: by reaction with the corresponding azidoformate in an aqueous-organic medium, in the presence of an alkali metal bicarbonate, if $R_1$ is 2-(diphenyl-4-yl)-isopropoxycarbonyl: by analogy with the method described in Helv. Chim. Acta, 51, 924 (1968), if $R_1$ is a radical of the general formula (V): by applying the method described by A. MORIMOTO et al., J. C. S. Perkin I, 1,109 (1980), starting from the corresponding halides [which can themselves be obtained according to Houben Weyl, Methoden der Organischen Chemie (Methods of Organic Chemistry), Volume 12, part 2, page 274, Georg Thieme Verlag Stuttgart (1964)], if $R_1NH$ is replaced by dimethylaminomethyleneamino: by analogy with the method described by J. F. FITT, J. Org. Chem. 42(15), 2,639 (1977), if $R_1NH$ is replaced by 4-nitrobenzylideneamino or 3,4-dimethoxybenzylideneamino: in accordance with the method described by R. A. FIRESTONE, Tetrahedron Lett., 375 (1972), if $R_2$ is methoxymethyl: according to S. SEKI et al., Tetrahedron Lett., 33, 2,915 (1977), if $R_2$ is t-butyl: according to R. J. STEDMAN, J. Med. Chem., 9, 444, (1966), if $R_2$ is benzhydryl: according to Dutch patent application No. 73/03,263, or if $R_2$ is benzyl, nitrobenzyl or p-methoxybenzyl: according to R. R. CHAUVETTE et al., J. Org. Chem., 38(17), 2,994 (1973).

The cephalosporin derivatives of the general formula (VIII) in which $R_1$ and $R_2$ are defined as above under (b) can be obtained by acylating a product of the general formula (X) in which $R_2$ is defined as under (b), by applying the methods described in French patent application No. 2,321,294.

The 7-aminocephalosporins of the general formula (X) in which $R_2$ is defined as under (b) can be obtained by application of or by analogy with the methods described by E. H. FLYNN, Cephalosporins and Penicillins, Ac. Press (1972).

The acids of the general formula (XI) in which $R_5$ is hydrogen or alkyl can be prepared in accordance with the method described in Belgian Pat. No. 850,662.

The products of the general formula (XI) in which $R_5$ is a vinyl radical can be prepared in accordance with the method described in Belgian Pat. No. 869,079.

The products of the general formula (XI) in which $R_5$ is a cyanomethyl radical can be prepared in accordance with the method described in German patent application No. 2,812,625.

The acids of the general formula (XI) in which $R_5$ is a protective radical can be prepared by protecting the oxime of an acid of this type in which $R_5$ is hydrogen, by any known method which does not affect the rest of the molecule. The protection is effected in particular by trityl or tetrahydropyranyl groups, which can be removed by acidolysis, e.g. by means of trifluoroacetic acid, formic acid (aqueous or non-aqueous) or p-toluenesulphonic acid. The protection can also be effected by the 2-methoxyprop-2-yl group, which can be removed by applying the method described in Belgian Pat. No. 875,379.

The acids of the general formula (XI) in which $R_5$ is a radical of the general formula (II') can be prepared in accordance with the methods described in Belgian Pat. Nos. 864,810, 865,298, 876,541 and 876,542.

The new products of the general formula (I) are useful as intermediates for the preparation of cephalosporins of the general formula:

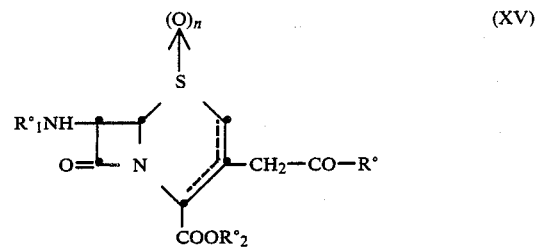

(XV)

in which $R°_1$ is defined in the same way as $R_1$ under (a) in the general formula (I), or represents a hydrogen atom or a radical of the general formula (II) in which the radical $R^c_5$ contained in $R_5$ is a hydrogen atom, and $R°_2$ is defined in the same way as $R_2$ under (a) in the general formula (I), or represents a hydrogen atom, or alternatively $R°_1$ and $R°_2$ are defined in the same way as $R_1$ and $R_2$ were defined above under (b), or represent hydrogen atoms, $R°$ is defined as above under (a) or (b) and n is equal to 0 or 1, and which are in the form of a 3-(2-oxoethyl)-bicyclooct-2-ene or -bicyclooct-3-ene if n=0, and in the form of a 3-(2-oxoethyl)-bicyclooct-2-ene if n=1.

The products of the general formula (XV) can be obtained from the products of the general formula (I) by the following procedure:

(1) If it is desired to prepare a product of the general formula (XV) in which $R°_1$ is other than a hydrogen atom and n=0, the enamine of the general formula (I), or a mixture of its isomers, is hydrolysed in an acid or neutral medium, and then, if appropriate, the acid-protecting radicals $R^c_5$ and/or $R_2$ are removed (in order to obtain a product in which $R°_1$ contains a free carboxyl radical and/or $R°_2$ is a hydrogen atom), and, if necessary, the protective radicals contained in $R°_1$ such as defined for $R_1$ under (b) are removed.

The reaction is preferably carried out in an organic acid (e.g. formic acid or acetic acid) or a mineral acid (e.g. hydrochloric acid or sulphuric acid), in the presence or absence of a solvent, in an aqueous or organic medium, at a temperature between −20° C. and the reflux temperature of the reaction medium, and this is followed, if appropriate, by treatment with an inorganic base (alkali metal bicarbonate) or an organic base (tertiary amine or pyridine).

If the reaction is carried out in an organic medium, the hydrolysis is performed by adding water to the reaction mixture.

If the reaction is carried out in the presence of a solvent, it is not necessary for the solvent to be miscible with the acid aqueous base. Contact is then effected by vigorous stirring.

Amongst the solvents which can be used, there may be mentioned chlorinated solvents, ethyl acetate, tetrahydrofuran, acetonitrile, dimethylformamide and alcohols.

It is not absolutely necessary to have purified the intermediate of the general formula (I) in order to carry out this reaction.

If it is desired to obtain a product of the general formula (XV) in which $R°_2$ is a hydrogen atom, the removal of the protective groups of the carboxyl radical is carried out:

in the case of a t-butyl, p-methoxybenzyl or benzhydryl group: by treatment in an acid medium; in the case of the benzhydryl radical, the reaction can be carried out in the presence of anisole;

in the case of a methoxymethyl group: by treatment in a dilute acid medium; or in the case of a nitrobenzyl group: by reduction (in particular treatment with zinc in acetic acid or hydrogenolysis).

If it is desired to prepare a product of the general formula (XV) in which $R°_2$ is a hydrogen atom and $R°_1$ is a radical of the general formula (II) in which $R_5$ is a group of the general formula (II'), the acid group of which is protected, it is necessary to use an enamine of the general formula (I) in which $R_2$ and $R^c_5$ are different and can be removed selectively. The same applies if it is desired, conversely, to prepare a ketone of the general formula (XV) in which $R°_1$ contains a free carboxyl group and $R°_2$ is other than a hydrogen atom.

If it is desired to remove the protective groups contained in $R°_1$ such as defined above for $R_1$ under (b), the reaction is carried out as described in French Patent Application No. 2,321,294.

(2) If it is desired to prepare a product of the general formula (XV) in which $R°_1$ is other than a hydrogen atom and n=1, the corresponding product of the general formula (XV) in which n=0 is oxidised. The reaction is carried out by applying the methods described in German Patent Application No. 2,637,176.

(3) If it is desired to prepare a ketone of the general formula (XV) in which $R°_1$ is a hydrogen atom, the radical $R°_1$ is removed from a product of the general formula (XV) [in which either $R°_1$ is defined in the same way as $R_1$ under (a), except that it cannot represent a radical of the general formula (II), or $R°_1$ represents a trityl radical, an alkoxycarbonyl radical (the alkyl part of which contains 1 to 5 carbon atoms), which is preferably branched on the carbon atom in the α-position to the oxygen atom and/or optionally substituted, or a phenoxyacetyl or phenacetyl radical, and $R°_2$ has one of the corresponding definitions given for $R_2$ under (a) or under (b), or represents a hydrogen atom], or alternatively the radicals $R°_1$ and $R°_2$ are simultaneously removed from a product of the general formula (XV) [in which $R°_1$ is defined as above and $R°_2$ has one of the corresponding definitions for $R_2$ under (a) or the definition, given for $R_2$ under (b), of a group which can easily be removed, e.g. p-nitrobenzyl or a substituted methyl group such as t-butyl or diphenylmethyl].

The removal of the protective radicals is carried out by any known method for freeing an amine and/or acid group, which does not affect the rest of the molecule.

The reaction is carried out in particular under the conditions described in French Patent Application No. 2,321,294.

By way of example:

The removal of the amine-protecting groups is carried out:

if $R°_1$ represents t-butoxycarbonyl, trityl or p-methoxybenzyloxycarbonyl: by treatment in an acid medium. Preferably, trifluoroacetic acid is used, the reaction being carried out at a temperature between 0° and 20° C., or alternatively formic, phosphoric or polyphosphoric acid is used, pure or in the presence of water, at a temperature between 20° and 60° C., or paratoluenesulphonic or methanesulphonic acid is used, in acetone or acetonitrile, at a temperature between 20° C. and the reflux temperature of the reaction mixture;

if $R°_1$ represents phenylacetyl or phenoxyacetyl: in accordance with the method described in Belgian Pat. No. 758,800;

if $R°_1$ represents benzyloxycarbonyl: by catalytic hydrogenation;

if $R°_1$ represents diphenylmethoxycarbonyl, 2-(biphenyl-4-yl)-isopropoxycarbonyl or vinyloxycarbonyl and if $R'_1NH$— is replaced by dimethylaminomethyleneamino, 3,4-dimethoxybenzylideneamino or 4-nitrobenzylideneamino: by hydrolysis in an acid medium;

if $R°_1$ represents a diphenylphosphinoyl radical: in accordance with the method described by P. HAAKE et al., J. Amer. Chem. Soc., 95, 8,073 (1973); or if $R°_1$ represents a radical $(Z'O)_2P(O)$—: in accordance with the method described in Belgian Pat. No. 833,619, or if $Z'$ is 2,2,2-trichloroethyl or p-nitrobenzyl: by reduction (in particular with zinc in acetic acid).

(4) If it is desired to prepare a product of the general formula (XV) in which $R°_1$ is a radical of the general formula (II), if necessary containing a free or protected acid group, and $R°_2$ has a definition given above for $R_2$ under (a), or represents a hydrogen atom, or alternatively $R°_1$ and $R°_2$ have the definitions given under (b) or $R°_2$ represents a hydrogen atom, and $R°$ has a corresponding definition given for $R_2$ under (a) or (b) and n is 0 or 1, it is also possible to acylate a 7-aminocephalosporin (or, if necessary, a mixture of its isomers) of the general formula (XV) in which, $R°$, $R°_2$ and n being defined as above, $R°_1$ is a hydrogen atom, by means of an acid represented by the general formula:

$$R°_1—OH \qquad \text{(XVI)}$$

in which $R°_1$ is defined as above, or by reaction with a reactive derivative of this acid, and then, if appropriate, to remove the protective radicals.

The reaction is carried out by analogy with the method described above for the preparation of the products of the general formula (VIII) from the products of the general formulae (X) and (XI), or under the conditions mentioned in French Patent Application No. 2,321,294.

It is understood that if $R°_1$ contains an amino or acid radical, the latter is protected beforehand.

If $R°_1$ contains a hydroxyimino, hydroxyl or sulpho group, the latter is free or protected.

These radicals are or can be protected in accordance with the methods described in French Patent Application No. 2,321,294.

By way of example:

the amine groups are protected by a protective group such as mentioned above for $R_6$, the acid groups are protected by a protective group such as defined above for $R_2$, and the oxime can be protected by a protective group such as mentioned above for $R_5$.

The removal of these radicals is carried out under the conditions described above; in particular, for the amine-protecting groups, it is carried out:

in the case of a benzyl or dibenzyl radical: by catalytic hydrogenation, or in the case of a p-nitrobenzyloxycarbonyl radical: by reduction, in particular treatment with zinc in acetic acid, or by hydrogenolysis.

The removal of the oxime-protecting radicals is carried out:

in the case of the trityl or tetrahydropyranyl radical: by acidolysis, e.g., by means of trifluoroacetic acid, aqueous or non-aqueous formic acid or para-toluenesulphonic acid, or in the case of the 2-methoxyprop-2-yl radical: in accordance with the method described in Belgian Pat. No. 875,379.

The cephalosporin derivatives of the general formula (XV) in which $R°_1$ and $R°_2$ are defined as under (b) or represent hydrogen atoms, $R°$ is defined as under (b) and n is defined as above are described for the antibacterial properties, or as intermediates for the preparation of products possessing antibacterial activity, in French Patent Application No. 2,321,294.

The products of the general formula (XV) in which $R°_1$, which will be referred to below as $R°_{1a}$, is defined in the same way as $R_1$ under (a), or represents a radical of the general formula (II) in which the symbol $R^c_5$ contained in $R_5$ is a hydrogen atom, $R°_2$, which will be referred to below as $R°_{2a}$, is defined in the same way as $R_2$ under (a), or represents a hydrogen atom, n is defined as above and $R°$ is defined as under (a) are intermediates for the preparation of products of the general formula:

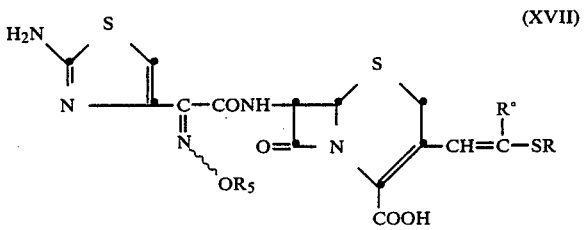

which possess antibacterial activity.

In the general formula (XVII), $R°$ is defined as above under (a), $R_5$ is a hydrogen atom or an alkyl, vinyl or cyanomethyl radical, or represents a group of the general formula (II') in which, $R^a_5$ and $R^b_5$ being defined as under (a), $R^c_5$ is a hydrogen atom, and R is chosen from amongst the following meanings:

(1) optionally N-oxidised pyrid-2-yl, pyrid-3-yl or pyrid-4-yl, (2) pyrimidin-2-yl, (3) 6-methylpyridazin-3-yl-1-oxide, (4) 5,6-dioxo-1,4,5,6-tetrahydro-1,2,4-triazin-3-yl substituted in the 4-position by (a) an alkyl radical containing 1 or 2 carbon atoms, which is optionally substituted by an alkoxy, alkylthio or formyl radical, (b) an allyl, 2,3-dihydroxypropyl, 1,3-dihydroxyprop-2-yl or 2-formyl-2-hydroxyethyl radical, or (c) an alkyl radical containing 2 or 3 carbon atoms, which is substituted by hydroxyl, carbamoyloxy, acyloxy or acylamino (the acyl portions of which are unsubstituted or substituted by amino), alkylsulphonylamino, ureido, alkylureido or dialkylureido, (5) 5,6-dioxo-1,4,5,6-tetrahydro-1,2,4-triazin-3-yl substituted in the 1-position, or 5,6-dioxo-1,2,5,6-tetrahydro-1,2,4-triazin-3-yl substituted in the 2-position, by an alkyl radical containing 1 or 2 carbon atoms, which is optionally substituted by a formyl radical, (6) 2-alkyl-2,5-dihydro-5-oxo-1,2,4-triazin-3-yl optionally substituted in the 6-position by an alkyl or alkoxy radical, the alkyl portions and radicals of which contain 1 or 2 carbon atoms, (7) 1-amino-1,2-dihydro-2-oxopyrimidin-4-yl, (8) 1,3,4-thiadiazol-5-yl substituted by alkyl, dialkylaminoalkyl or acylaminoalkyl, (9) tetrazol-5-yl substituted in the 1position by (a) an alkyl radical containing 1 or 2 carbon atoms, which is optionally substituted by a formyl radical, or (b) an alkyl radical containing 2 or 3 carbon atoms, which is substituted by hydroxyl, acylamino or dialkylamino, or

(10) (a) 1-alkyl-1,2,4-triazol-5-yl optionally substituted in the 3-position by an alkoxycarbonyl radical, the alkyl and alkoxy radicals of which contain 1 or 2 carbon atoms, or (b) 1-alkyl-1,3,4-triazol-5-yl.

It is understood that the substituents $R°$ and —SR can be located respectively in the E and Z position, and vice versa, relative to the cephalosporin nucleus, and that these isomers and mixtures thereof fall within the definition of the general formula (XVII).

Likewise, the radical —$OR_5$ can be in the syn or anti positions and these isomers and mixtures thereof also fall within the definition of the general formula (XVII).

If the radical R is a 1,4,5,6-tetrahydrotriazinyl radical substituted in the 1- or 4-position or a 1,2,5,6-tetrahydrotriazinyl radical substituted in the 2-position, it can be represented by the tautomeric forms:

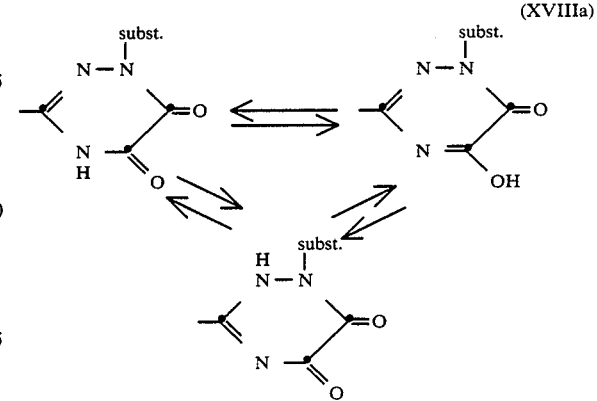

-continued

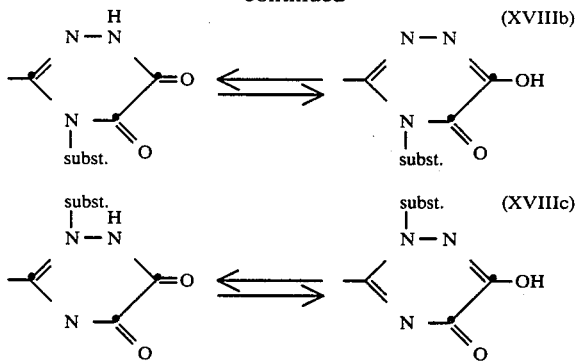

If the radical R contains a formylalkyl substituent, it can be in the form of the free aldehyde or the aldehyde hydrate. These forms are observed in particular under the conditions described below.

Nuclear magnetic resonance studies show in particular that if R is 5,6-dioxo-4-formylmethyl-1,4,5,6-tetrahydro-1,2,4-triazin-3-yl:

in an acid solvent such as (deuterated) formic or trifluoroacetic acid, in the presence or absence of (heavy) water, the product is mainly in the form of the free aldehyde;

in a basic solvent such as (heavy) water to which sodium bicarbonate has been added, it is mainly in the form of the aldehyde hydrate; and in a neutral solvent such as dimethyl sulphoxide (d$_6$), the free aldehyde and aldehyde hydrate forms are present, the addition of water displacing the equilibrium in favour of the aldehyde hydrate form.

The products of the general formula (XVII) can be obtained from the ketones of the general formula (XV) by the following procedure:

The cephalosporins of the general formula:

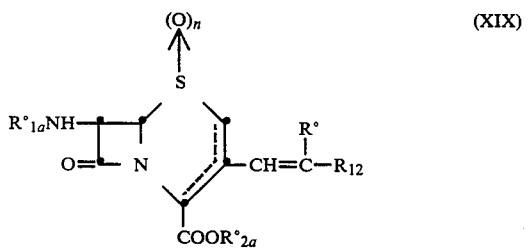

[in which $R°_{1a}$, $R°_{2a}$ and n are defined as above or $R°_{1a}$ is a radical of the general formula (II) in which $R^c_5$ and/or $R_6$ are hydrogen atoms, $R°$ is defined as above under (a), it being understood that if n=0, the product is in the form of a bicyclooct-2-ene and/or bicyclooct-3-ene, and if n=1, the product is in the form of a bicyclooct-2-ene, and the symbol $R_{12}$ represents a radical of the general formula:

$$R'_{12}SO_2O— \qquad (XX)$$

in which $R'_{12}$ represents an alkyl radical, a trihalogenomethyl radical (e.g. trifluoromethyl) or a phenyl radical optionally substituted by a halogen atom or by one or more alkyl or nitro radicals] can be prepared by reacting an activated form of an acid $R'_{12}SO_3H$, of the type:

$$(R'_{12}SO_2)_2O \qquad (XXa)$$

$$R'_{12}SO_2Hal \qquad (XXb)$$

[$R'_{12}$ being defined as above and Hal being a halogen atom] with a ketone of the general formula (XV) such as defined for the intermediates of the products of the general formula (XVII), or with a mixture of its isomers, this being followed, if appropriate, by the reduction of the sulphoxide obtained if n=1, and, if appropriate, by the removal of the protective radicals of the amine group of the radical of the general formula (II) and/or of the acid groups.

It is understood that if $R°_{1a}$ is a radical of the general formula (II) in which $R_5$ is a hydrogen atom, it is necessary for the oxime to be protected. The protection and the removal are carried out in accordance with the methods described above.

The reaction is generally carried out in the presence of a tertiary base of the general formula:

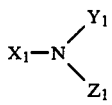

in which $X_1$, $Y_1$ and $Z_1$ represent alkyl or phenyl radicals or, if appropriate, two of them form a ring with the nitrogen atom to which they are attached (e.g. triethylamine or dimethylaniline), or a pyridine substituted by alkyl or dialkylamino radicals (e.g. 2,6-di-t-butyl-4-methylpyridine), or a lithium amide obtained by reacting an alkyllithium (e.g. n-butyllithium) with a secondary amine of the general formula:

in which $X_2$ and $Y_2$ represent alkyl or phenyl radicals, or, if appropriate, $X_2$ and $Y_2$ form a ring with the nitrogen atom to which they are attached (e.g. diisopropylamine or 2,2,6,6-tetramethylpiperidine), or an alkali metal alcoholate (e.g. potassium t-butylate), or an alkali metal hydride (e.g. potassium hydride), or an alkyllithium or an aryllithium (e.g. n-butyllithium or mesyllithium), in an organic solvent such as an ether (e.g. dioxane, tetrahydrofuran, or 1,2-dimethoxyethane), or in a mixture of organic solvents comprising an ether (such as mentioned above) and a solvent such as hexamethylphosphorotriamide, N-methylpyrrolidone or 1,3-dimethylimidazolidin-2-one, at a temperature between −78° C. and the reflux temperature of the reaction mixture, if appropriate under an inert atmosphere (nitrogen or argon).

If necessary, the reduction of the S-oxide is carried out in accordance with the methods described in German Patent Application No. 2,637,176.

The removal of the amine-protecting and acid-protecting radicals is carried out under the conditions described above.

It is also possible to obtain the products of the general formula:

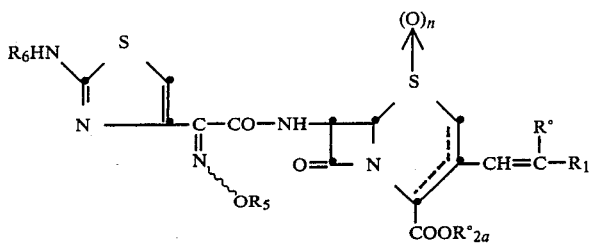

(XXII)

[in which, $R_5$, $R°_{2a}$, $R°$, $R_{12}$ and n being defined as above, if n=0, the product is in the form of a bicyclooct-2-ene or bicyclooct-3-ene, and if n=1, the product is in the form of a bicyclooct-2-ene, and $R_6$ and $R^c_5$ (contained in $R_5$) are defined as above under (a), or represent hydrogen atoms] by the following procedure:

A 7-aminocephalosporin of the general formula:

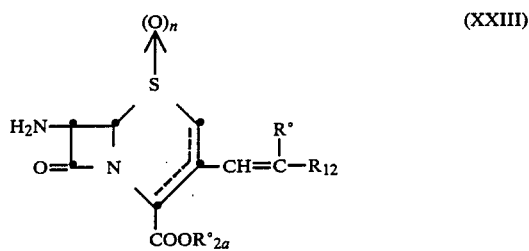

(XXIII)

[in which $R°_{2a}$, $R_{12}$ and n are defined as above and the position of the double bond and the configuration of the substituent in the 3-position are the same as for the product of the general formula (XIX)] is prepared by removing the radical $R°_{1a}$, or, if appropriate, simultaneously removing the protective radicals $R°_{1a}$ and $R°_{2a}$, from a product of the general formula (XIX) [in which $R°_{1a}$ is defined in the same way as $R_1$ was defined above under (a), except that it cannot represent a radical of the general formula (II)].

The reaction is carried out under the conditions described above for the preparation of a product of the general formula (XV) in which $R°_1$ is a hydrogen atom.

It is then possible to prepare the products of the general formula (XXII) by acylating the 7-aminocephalosporin of the general formula (XXIII) (or, optionally, a mixture of its isomers) by means of an acid of the general formula (XI), or by reaction with a reactive derivative of this acid, and then, if appropriate, reducing the sulphoxide obtained and, if appropriate, removing the protective radicals.

The reaction is carried out under the conditions described above for the preparation of a 7-aminocephalosporin of the general formula (VIII), the blocking conditions being the same.

If necessary, the reduction of the sulphoxide and the removal of the acid-protecting and/or amine-protecting radicals are carried out under the conditions described above.

I. The 3-thiovinylcephalosporins of the general formula (XVII) can be prepared by reacting a thiol (or one of its alkali metal or alkaline earth metal salts) of the general formula:

R—SH  (XXIV)

(in which R, which is defined as above, is optionally protected) with a cephalosporin derivative (or a mixture of the isomers) of the general formula (XXII), such as defined above, this being followed by the reduction of the sulphoxide obtained if n=1, and, if necessary, by the removal of the protective radicals.

If it is desired to obtain a product of the general formula (XVII) in which R contains a formyl radical, a thiol of the general formula (XXIV) is used, in which this radical is protected in the form of an acetal of the general formula:

(XXVa)

or

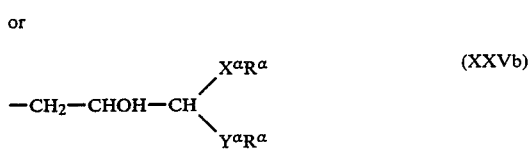

(XXVb)

in which formulae alk is an alkylene radical containing 1 or 2 carbon atoms, $X^\alpha$ and $Y^\alpha$ are identical and represent oxygen or sulphur atoms and $R^\alpha$ represents an alkyl radical, or alternatively $X^\alpha$ and $Y^\alpha$ are identical or different and represent oxygen or sulphur atoms and the radicals $R^\alpha$ together form an alkylene radical containing 2 or 3 carbon atoms.

It is understood that if the radical R of the product of the general formula (XXIV) is capable of interfering with the reaction, it is preferable to protect this group by any method which is in itself known and which does not affect the rest of the molecule.

In the case of an amino or alkylamino group, the protection is effected by a radical such as $R_6$ defined above.

In the case of hydroxyl groups, the protection is effected by trityl, tetrahydropyranyl or 2-methoxyprop-2-yl radicals, or alternatively, in the case of a 2,3-dihydroxypropyl or 1,3-dihydroxyprop-2-yl radical, as a cyclic acetal in the form of a 2,2-dimethyldioxolan-4-ylmethyl or 2,2-dimethyldioxan-5-yl radical.

Furthermore, it is understood that if the radical R of the product of the general formula (XXIV) contains a hydroxyl or sulphonyl radical, it is preferable to use a product of the general formula (XXII) in which n=0.

It is also understood that if the radical $R_5$ in the general formula (XXII) is a hydrogen atom, it is preferable to protect the oxime under the conditions described above.

The reaction of the products of the general formulae (XXIV) and (XXII) is generally carried out in the presence of a base such as a pyridine or a tertiary organic base of the general formula (XXIa). The base used is e.g. diisopropylethylamine or diethylphenylamine.

If a salt of the thiol of the general formula (XXIV) is used, it is not necessary to carry out the reaction in the presence of an organic base such as defined above.

The reaction is advantageously carried out in an organic solvent such as dimethylformamide, tetrahydrofuran, acetonitrile, or a mixture of such solvents.

It is also possible to carry out the reaction in the presence of an alkali metal bicarbonate, in a solvent such as mentioned above, if appropriate in the presence of water. The reaction is carried out at a temperature between −20° C. and the reflux temperature of the reaction mixture, the chosen temperature varying according to the thiol employed. Likewise, the reaction time can vary from 5 minutes to 48 hours, according to the thiol employed.

If appropriate, the reaction is carried out under nitrogen.

The reduction of the oxide and the removal of the amine-protecting, acid-protecting or oxime-protecting groups are carried out in accordance with the methods described above.

The removal of the protective radicals of hydroxyl groups is carried out under the conditions described above for the oxime-protecting radicals, i.e.:

by acidolysis, e.g. with trifluoroacetic acid, aqueous or non-aqueous formic acid or para-toluenesulphonic acid in the case of the trityl, tetrahydropyranyl, 2,2-dimethyldioxolan-4-yl-methyl or 2,2-dimethyldioxan-5-yl radical; if aqueous or non-aqueous formic acid is used, the freeing of the hydroxyl radicals protected in the form of a cyclic acetal can lead at least partially to the corresponding formic acid monoesters or diesters, which can be separated off by chromatography, if necessary; or in accordance with the method described in Belgian Pat. No. 975,379 in the case of the 2-methoxyprop-2-yl radical.

The removal of the groups of the general formula (XXVa) or (XXVb) (if it is desired to obtain a product of the general formula (XVII) in which R contains a formyl radical) is carried out:

in the presence of a sulphonic acid (e.g. methanesulphonic acid or p-toluenesulphonic acid), in an organic solvent (e.g. acetonitrile or acetone), if appropriate in the presence of water and if appropriate in the presence of a reagent which can be converted to an acetal, such as acetone, glyoxylic acid, benzaldehyde or pyruvic acid, at a temperature between 20° C. and the reflux temperature of the reaction mixture, or alternatively, if the radical R is a 5,6-dioxo-1,4,5,6-tetrahydro-1,2,4-triazin-3-yl radical, by reaction with pure formic acid or aqueous formic acid (preferably containing less than 10% of water), either in the presence or absence of silica, or by trans-acetalisation in the presence of a reagent which can be converted to an acetal, such as defined above.

It is frequently preferable to carry out the reaction by means of the sulphoxide of the cephalosporin of the general formula (XXII). In the opposite case, if a mixture of bicyclooct-2-ene and bicyclooct-3-ene isomers of the general formula (XVII) is obtained, this mixture can be oxidised in order to obtain the oxide of the corresponding product of the general formula (XVII), which is in the form of a bicyclooct-2-ene. This oxide can then be reduced in order to obtain the bicyclooct-2-ene isomer of the general formula (XVII).

The thiols of the general formula (XXIV) (which can be used in their tautomeric form) can be prepared by applying one of the following methods, depending on the meaning of the radical R:

if R is a pyrid-3-yl radical: in accordance with the method described by H. M. WUEST and E. H. SAKAL, J. Amer. Chem. Soc., 73, 1,210 (1951), if R is a pyrid-3-yl-1-oxide radical: in accordance with the method described by B. BLANK et al., J. Med. Chem. 17, 1,065 (1974), if R is a pyrid-4-yl-1-oxide radical: in accordance with the method described by R. A. Y. JONES et al., J. Chem. Soc. 2,937 (1960), if R is a 6-methylpyridazin-3-yl-1-oxide radical: in accordance with the method described in Belgian Pat. No. 787,635, or if R is 1°. a 5,6-dioxo-1,4,5,6-tetrahydro-1,2,4-triazin-3-yl radical substituted in the 4-position by a radical Rγ chosen from amongst:

(a) an allyl radical, an alkyl radical (containing 1 or 2 carbon atoms, which is itself optionally substituted by an alkoxy or alkylthio radical), (b) a 2,3-dihydroxypropyl or 1,3-dihydroxyprop-2-yl radical (optionally protected in the form of a cyclic acetal), (c) an alkyl radical [containing 2 or 3 carbon atoms, which is itself substituted by hydroxyl, carbamoyloxy, alkylsulphonylamino, acylamino (optionally substituted), ureido, alkylureido or dialkylureido], and (d) a radical of the general formula (XXVa) or (XXVb), or 2°. a 5,6-dioxo-1,4,5,6-tetrahydro-1,2,4-triazin-3-yl radical substituted in the 1-position, or a 5,6-dioxo-1,2,5,6-tetrahydro-1,2,4-triazin-3-yl radical substituted in the 2-position, by an alkyl radical containing 1 or 2 carbon atoms or by a radical of the general formula (XXVa): by reacting an alkyl oxalate with a thiosemicarbazide of the general formula:

| | |
|---|---|
| RγNHCSNH—NH₂ | (XXVIa) |
| H₂NCSNHNH—Rγ' | (XXVIb) | or

$$\begin{array}{l} H_2NCSN-NH_2 \\ \phantom{H_2NCS}| \\ \phantom{H_2NCSN}R\gamma' \end{array} \qquad (XXVIc)$$

in which formulae Rγ has the definition given above under 1°. and Rγ' is a substituent defined above under 2°., in the presence of an alkali metal alcoholate, e.g. sodium ethylate or methylate or potassium t-butylate, by applying the method described by M. PESSON and M. ANTOINE, Bull. Soc. Chim. France 1,590 (1970).

It is not absolutely necessary to purify the product obtained (or to free the protected radicals) in order to use it for the preparation of the products of the general formula (XVII).

The thiosemicarbazide of the general formula (XXVIa), (XXVIb) or (XXVIc) can be prepared in accordance with one of the methods described by K. A. JENSEN et al., Acta Chem. Scand., 22, 1 (1968), or by applying the method described by Y. KAZAKOV and J. Y. POTOVSKII, Doklady Acad. Nauk. SSSR 134, 824 (1960), it being understood that if Rγ contains an amino radical, the latter is protected.

The protection of the amino radical and the removal of the protective radical are carried out in accordance with the usual methods which do not affect the rest of the molecule. The t-butoxycarbonyl group, which can be removed by acid hydrolysis, is used in particular.

If R is 1-alkyl-1,3,4-triazol-5-yl radical: by applying one of the methods described by M. PESSON and M. ANTOINE, Bull. Soc. Chim. France 1,590 (1970).

If R is a 5,6-dioxo-1,4,5,6-tetrahydro-1,2,4-triazin-3-yl radical substituted in the 4-position by acyloxyalkyl (optionally substituted): by acylating 5,6-dioxo-4-hydroxyalkyl-3-mercapto-1,4,5,6-tetrahydro-1,2,4-triazine, the mercapto radical of which has been protected beforehand (e.g. according to C. G. KRUSE et al., Tet. Lett. 1,725 (1976)), by any known method for acylating an alcohol without affecting the rest of the molecule, and then freeing the mercapto group in an acid medium.

If R is a 2-alkyl-5,6-dioxo-1,2,5,6-tetrahydro-1,2,4-triazin-3-yl, 1-alkyl-1,2,4-triazol-5-yl or 1-alkyl-3-alkoxycarbonyl-1,2,4-triazol-5-yl radical: in accordance with the method described by M. PESSON and M. ANTOINE, C.R. Acad. Sci., Ser C, 267, 25, 1,726 (1968).

If R is a 2-alkyl-2,5-dihydro-5-oxo-1,2,4-triazin-3-yl radical substituted in the 6-position by an alkyl or alkoxy radical: in accordance with the method described in J. Antibiotics, 33, 783 (1980).

If R is a 1-amino-1,2-dihydro-2-oxopyrimidin-4-yl radical: in accordance with the method described in European patent application No. 00,005.

If R is a 1,3,4-thiadiazol-5-yl radical optionally substituted by alkyl: in accordance with the methods described in Belgian Pat. No. 830,821.

If R is a 1,3,4-thiadiazol-5-yl radical substituted by dialkylaminoalkyl: in accordance with the method described in German patent application No. 2,446,254.

If R is a 1,2,4-thiadiazol-5-yl radical substituted by an acylaminoalkyl radical: in accordance with the method described in Japanese patent application No. 76/80,857.

If R is a tetrazol-5-yl radical optionally substituted in the 1-position by alkyl or hydroxyalkyl: in accordance with the methods described in Belgian Pat. No. 830,821.

If R is a tetrazol-5-yl radical substituted in the 1-position by a dialkylaminoalkyl radical: by applying the method described in German patent application No. 2,738,711.

If R is a tetrazol-5-yl radical substituted by an acylaminoalkyl radical: in accordance with the method described in U.S. Pat. No. 4,117,123.

If R is a tetrazol-5-yl radical substituted in the 1-position by a radical of the general formula (XXVa): by reacting sodium azide with the corresponding isothiocyanate, by analogy with the method described by R. E. ORTH, J. Pharm. Sci. 52 (9), 909 (1963).

II. The thiovinylcephalosporins of the general formula (XVII) can also be obtained in the following manner:

A thiol of the general formula (XXIV) (or one of its alkali metal or alkaline earth metal salts) is reacted with a product of the general formula (XIX) (or with a mixture of its isomers) [in which $R°_{1a}$ is defined in the same way as $R_1$ under (a), except that it cannot represent a radical of the general formula (II)], and then, if appropriate, the sulphoxide obtained (if n=1) is reduced and, if appropriate, the protective radicals of R are removed in order to prepare a product of the general formula:

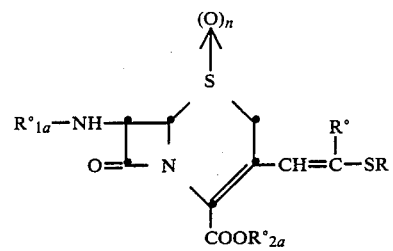

(XXVII)

in which, n being defined as above, $R°$, $R°_{1a}$ and $R°_{2a}$ are defined as above and R assumes a corresponding definition.

The reaction is carried out under the conditions described above for the preparation of a product of the general formula (XVII) from a product of the general formula (XXII) and a thiol of the general formula (XXIV).

It is understood that (if necessary) the radical R of the thiol is protected as described above, and that the removal of the protective radicals can be carried out under the conditions described above. However, it is preferable to retain the protective groups until the product of the general formula (XVII) has been obtained.

It is frequently preferable to employ a product of the general formula (XIX) in which n=1. In the opposite case, if a mixture of bicyclooct-2-ene and bicyclooct-3-ene isomers is obtained, it is necessary to convert the product to the sulphoxide for the remainder of the operations, which has the effect of stabilising the double bond so as to give a bicyclooct-2-ene, and then to reduce the sulphoxide of the final product obtained.

A product of the general formula:

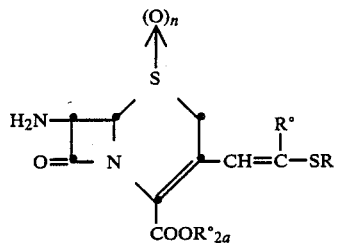

(XXVIII)

in which R, $R°$, $R°_{2a}$ and n are defined as above, is prepared by removing the radical $R°_{1a}$ from a product of the general formula (XXVII), such as defined above, or, if appropriate, simultaneously removing the radical $R°_{1a}$ and the other protective radicals from this product.

The reaction is carried out under the conditions described above for the preparation of a product of the general formula (XXIII). It is not necessary to isolate the product of general formula (XXVIII) for use in the following synthesis.

The 3-thiovinylcephalosporin of the general formula (XVII) is then prepared by acylating a 7-amino-cephalosporin of the general formula (XXVIII) in which R, $R°$ and $R°_{2a}$ are defined as above, by means of an acid represented by the general formula (XI) [in which $R_5$ and $R_6$ are defined as above], or a reactive derivative of this acid, under the conditions described above for the preparation of the products of the general formula (VIII), and the oxide obtained (if n=1) is then reduced and the protective radicals are removed.

It is understood that:

the amino or alkylamino radicals which exist in certain radicals R must be protected, and the carboxyl, hydroxyl or formyl radicals contained in the radicals R can be protected.

The protection, and the removal of the protective radicals, and also the reduction of the oxide, are carried out under the conditions described above.

It is also understood that if R contains a hydroxyl or sulphonyl substituent, it is preferred to use a product of the general formula (XXVIII) in which n=0.

The products of the general formulae (XIX), (XXII) or (XXVII) in which n=1 can be obtained by oxidising the corresponding products in which n=0, in accordance with the method described in German patent application No. 2,637,176.

The isomers of the products of the general formulae (I), (XV), (XVII), (XIX), (XXII), (XXIII), (XXVII) and (XXVIII) can be separated by chromatography or by crystallisation.

More particularly, the bicyclooct-2-ene isomers of the products of the general formula (XV), (XVII), (XIX), (XXII) or (XXVII) can be obtained frowm the bicyclooct-2-ene+bicyclooct-3-ene mixtures by oxidation and then reduction.

The products of the general formula (XVII) can be converted to addition salts with acids. They can also be converted to metal salts or to addition salts with nitrogen-containing bases in accordance with the methods which are in themselves known.

The new products according to the invention and the products of the general formulae (XV) and (XVII) can be purified, if appropriate, by physical methods such as crystallisation or chromatography.

The cephalosporin derivatives of the general formula (XVII) and their pharmaceutically acceptable salts possess particularly valuable antibacterial properties. They show a remarkable in vitro and in vivo activity against Gram-positive and Gram-negative germs.

In vitro, they have been shown to be active at a concentration of between 2 and 20 μg/cc against staphylococcus strains sensitive to penicillin G (*Staphylococcus aureus* Smith) and at a concentration of between 1 and 10 μg/cc against *Escherichia coli*, NIHJ strain.

In vivo, they have been shown to be active at a daily dose of between 1 and 20 mg/kg, administered subcutaneously, against experimental infections caused in mice by *Staphylococcus aureus* Smith (sensitive to penicillin G), and at daily doses of between 0.01 and 10 mg/kg, administered subcutaneously, against experimental infections caused in mice by *Escherichia coli* (Monod strain). Furthermore, the $LD_{50}$ of the compounds of general formula (XVII) is between 1.5 and doses greater than 2.5 g/kg by subcutaneous administration in the mouse.

Of particular value are the products of the general formula (I) in which the symbol $R_1$ is a trityl radical, a radical of the general formula (III), a radical of the general formula (IV) or a radical of the general formula (V) and the symbol $R_2$ is a protective radical such as defined under (a), or alternatively the symbol $R_1$ is a radical of the general formula (VI) and the symbol $R_2$ is a protective radical such as defined under (b), the symbol $R°$ represents an alkyl or phenyl radical and the symbols $R_3$ and $R_4$ represent alkyl radicals, and amongst these products, those which are more especially valuable are the products of the general formula (I) in which the symbol $R_1$ is a trityl radical, a radical of the general formula (III) in which $R_7$ is phenoxymethyl, a radical of the general formula (IV) in which $R_8$ is a branched alkyl radical, a radical of the general formula (V) in which Z is an alkoxy radical, or an α-amino-α-phenylacetamido radical, the amide group of which is protected, the symbol $R_2$ is a benzhydryl or p-methoxybenzyl radical, the symbol $R°$ is methyl or phenyl and the symbols $R_3$ and $R_4$ are methyl radicals.

The following examples, which are given without implying a limitation, illustrate the present invention.

EXAMPLE 1

1-Dimethylamino-1-methoxyethylene (2.02 g) is added dropwise, in the course of 50 minutes, to a solution of 2-benzhydryloxycarbonyl-7-t-butoxycarbonylamino-3-methyl-8-oxo-5-thia-1-azabicyclo[4.2.0]oct-2-ene (2.4 g) in dimethylformamide (10 cc) at 80° C. The mixture is concentrated to dryness under reduced pressure (1 mm Hg; 0.13 kPa) at 30° C. The residue is dissolved in ethyl acetate (10 cc) and the solution is filtered on basic alumina (50 g). Elution is carried out with ethyl acetate (200 cc) and the eluate is concentrated to dryness under reduced pressure (20 mm Hg; 2.7 kPa) at 20° C. This yields a 50/50 mixture of the Z and E forms of 2-benzhydryloxycarbonyl-7-t-butoxycarbonylamino-3-(2-dimethylaminoprop-1-en-1-yl)-8-oxo-5-thia-1-azabicyclo[4.2.0]oct-2-ene (1 g) in the form of a red oil.

Infra-red spectrum ($CCl_4$), characteristic bands ($cm^{-1}$): 3,440, 1,770, 1,720, 1,505, 1,370, 1,160, 700.

Proton NMR spectrum (350 MHz, $CDCl_3$, δ in ppm, J in Hz); mixture of the Z and E isomers: 1.45 (s, —C(CH$_3$)$_3$); 1.88 and 1.94 (2s,

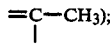

2.85 and 2.86 (2s, —N(CH$_3$)$_2$); 3.05 to 3.35 (m, —S—CH$_2$—); 5.05 (d, J=4, —H in the 6-position); 5.32 (m, —H in the 7-position); 5.50 (d, J=9, —CONH—); 5.83 and 6.03 (2s, —CH=); 6.89 (s, —COOCH(C$_6$H$_5$)$_2$).

EXAMPLE 2

A solution of tris-dimethylaminomethylbenzene (1.9 g) in dioxane (15 cc) is added, in the course of 3 minutes, to a solution of 2-benzhydryloxycarbonyl-7-t-butoxycarbonylamino-3-methyl-8-oxo-5-thia-1-azabicyclo[4.2.0]oct-2-ene (1.08 g) in dioxane (15 cc) at 80° C., whilst keeping the temperature at 80° C., and stirring is then continued at this temperature for 15 minutes. The reaction mixture is poured into a stirred mixture of ethyl acetate (100 cc) and water (100 cc) and crushed ice. The organic phase is separated off, washed with water (2× with 50 cc) and dried over magnesium sulphate and the solvent is evaporated off to dryness under reduced pressure (20 mm Hg; 2.7 kPa) at 20° C. The residue is chromatographed on a column of Merck silica gel (0.04–0.06) (200 g) (diameter of the column: 4 cm, height: 32 cm). Elution is carried out with a 20/80 (by volume) ethyl acetate/cyclohexane mixture (1.5 liters) under a pressure of 40 kPa, 50 cc fractions being collected. Fractions 19 to 26 are combined and concentrated to dryness under reduced pressure (20 mm Hg; 2.7 kPa) at 20° C. This yields the E form of 2-benzhydryloxycarbonyl-7-t-butoxycarbonylamino-3-[α-(β-dimethylaminostyryl)]-8-oxo-5-thia-1-azabicyclo[4.2.0]oct-2-ene (0.4 g) in the form of a yellow solid.

Infra-red spectrum (CHCl₃), characteristic bands (cm⁻¹): 3,430, 1,765, 1,715, 1,575, 1,540, 1,500, 1,495, 1,450, 1,390, 1,370, 1,150, 690.

Proton NMR spectrum (350 MHz, CDCl₃, δ in ppm, J in Hz): 1.48 (s, 9H, (CH₃)₃C—); 2.30 and 2.40 (2d, J=14, 2H, —CH₂—S—); 2.83 (s, 6H, —N(CH₃)₂); 4.97 (d, J=4, 1H, H in the 6-position); 5.20 (d, J=9, 1H, —CONH—); 5.27 (dd, J=4 and 9, 1H, H in the 7-position); 6.61 (s, 1H, —CH=); 6.92 (s, 1H, —COOCH<).

EXAMPLE 3

1-Dimethylamino-1-methoxyethylene (4 cc) is added, in the course of 55 minutes, to a solution of 7-t-butoxycarbonylamino-2-(4-methoxybenzyloxycarbonyl)-3-methyl-8-oxo-5-thia-1-azabicyclo[4.2.0]oct-2-ene (3.75 g) in dimethylformamide (25 cc), heated to 80° C., the temperature being kept at 80° C. This yields a solution of 7-t-butoxycarbonylamino-3-(2-dimethylaminoprop-1-en-1-yl)-2-(4-methoxybenzyloxycarbonyl)-8-oxo-5-thia-1-azabicyclo[4.2.0]oct-2-ene, which is poured into a mixture of iced water (20 cc) and ethyl acetate (150 cc). The organic phase is washed with water (2×200 cc), dried over sodium sulphate and filtered in the presence of decolorising charcoal and the filtrate is evaporated to dryness under reduced pressure (20 mm Hg; 2.7 kPa). The residue is chromatographed on a column of Merck silica gel (0.06–0.2) (45 g) (diameter of the column: 3 cm, height: 15 cm). Elution is carried out with a 20/80 (by volume) ethyl acetate/cyclohexane mixture (500 cc) and 40 cc fractions are collected. Fractions 7 to 10 are concentrated to dryness under reduced pressure (20 mm Hg; 2.7 kPa) and this yields a mixture (70/30) of 3-acetonyl-7-t-butoxycarbonylamino-2-(4-methoxybenzyloxycarbonyl)-8-oxo-5-thia-1-azabicyclo[4.2.0]oct-2-ene and -oct-3-ene (0.25 g) in the form of an ochre solid.

Rf=0.27, Merck silica plate F₂₅₄, thickness 0.25 mm, eluant: 40/60 (by volume) ethyl acetate/cyclohexane.

Mass spectrum: M=476.

Proton NMR spectrum (350 MHz, CDCl₃, δ in ppm, J in Hz): 1.47 (s, 9H, —C(CH₃)₃ of the oct-2-ene and the oct-3-ene); 2.03 (s, —CO—CH₃ of the oct-3-ene); 2.12 (s, —CO—CH₃ of the oct-2-ene); 3.18 and 3.33 (2d, J=17.5, —CH₂—CO— of the oct-3-ene); 3.30 and 3.55 (2d, J=18, —CH₂—S— of the oct-2-ene); 3.51 and 3.73 (2d, J=17.5, —CH₂—CO— of the oct-2-ene); 3.80 (s, —OCH₃ of the oct-2-ene); 3.82 (s, —OCH₃ of the oct-3-ene); 4.95 (d, J=4.5, —H in the 6-position of the oct-2-ene, and s, —H in the 2-position of the oct-3-ene); 5.07 (s, —COO—CH₂— of the oct-3-ene); 5.13 and 5.20 (2d, J=12, —COO—CH₂— of the oct-2-ene); 5.21 (d, J=4, —H in the 6-position of the oct-3-ene); 5.33 (d, J=9, —CO—NH— of the oct-2-ene); 5.42 (m, —CO—NH— and —H in the 7-position of the oct-3-ene); 5.59 (dd, J=9 and 4.5, —H in the 7-position of the oct-2-ene); 6.06 (s, —H in the 4-position of the oct-3-ene); 6.89 (m, aromatic —H atoms in the ortho-position to the —OCH₃ of the oct-2-ene and the oct-3-ene); 7.28 (d, J=7.5, aromatic —H atoms in the meta-position to the —OCH₃ of the oct-3-ene); 7.34 (d, J=7.5, aromatic —H atoms in the ortho-position to the —OCH₃ of the oct-2-ene).

EXAMPLE 4

1-Dimethylamino-1-methoxyethylene (4 cc) is added, in the course of 56 minutes, to a solution of an approximately 50/50 mixture of 2-benzhydryloxycarbonyl-3-methyl-8-oxo-7-tritylamino-5-thia-1-azabicyclo[4.2.0]oct-2-ene and -oct-3-ene (5.38 g) in dimethylformamide (25 cc), heated to 80° C., whilst keeping the temperature at 80° C. This yields a solution of a mixture of 2-benzhydryloxycarbonyl-3-(2-dimethylaminoprop-1-en-1-yl)-8-oxo-7-tritylamino-5-thia-1-azabicyclo[4.2.0]oct-2-ene and -oct-3-ene, which is poured into a mixture of iced water (200 cc) and ethyl acetate (200 cc). The organic phase is washed with water (2×200 cc), dried over sodium sulphate and filtered in the presence of decolorising charcoal and the filtrate is evaporated to dryness under reduced pressure (20 mm Hg; 2.7 kPa). The residue is chromatographed on a column of Merck silica gel (0.06–0.2) (60 g) (diameter of the column: 3 cm, height: 20 cm). Elution is carried out with a 15/85 (by volume) ethyl acetate/cyclohexane mixture (1,000 cc), 60 cc fractions being collected. Fractions 9 to 15 are combined and evaporated to dryness under reduced pressure (20 mm Hg; 2.7 kPa). This yields an approximately 50/50 mixture of 3-acetonyl-2-benzhydryloxycarbonyl-8-oxo-7-tritylamino-5-thia-1-azabicyclo[4.2.0]oct-2-ene and -oct-3-ene (0.51 g) in the form of a yellow solid.

Rf=0.18, Merck silica plate F₂₅₄, thickness 0.25 mm; eluant: 20/80 (by volume) ethyl acetate/cyclohexane.

Mass spectrum: M=664.

Proton NMR spectrum (350 MHz, CDCl₃, δ in ppm, J in Hz): 1.88 (s, —CO—CH₃ of the oct-3-ene); 2 (s, —CO—CH₃ of the oct-2-ene); 3 and 3.18 (2d, J=16, —CH₂—CO— of the oct-3-ene); 3.02 (d, J=11, >NH of the oct-3-ene); 3.11 and 3.34 (2d, J=18, —CH₂—S— of the oct-2-ene); 3.14 (d, J=8, >NH of the oct-2-ene); 3.44 and 3.66 (2d, J=17, —CH₂—CO— of the oct-2-ene); 4.23 (d, J=3.5, —H in the 6-position of the oct-3-ene); 4.31 (d, J=4.5, —H in the 6-position of the oct-2-ene); 4.58 (dd, J=3.5 and 11, —H in the 7-position of the oct-3-ene); 4.72 (dd, J=8 and 4.5, —H in the 7-position of the oct-2-ene); 5 (s, —H in the 2-position of the oct-3-ene); 5.89 (s, —H in the 4-position of the oct-3-ene); 6.70 (s, —COOCH(C₆H₅)₂ of the oct-3-ene); 6.85 (s, —COOCH(C₆H₅)₂ of the oct-2-ene); 7.15 to 7.60 (m, 25H, aromatic protons).

EXAMPLE 5

A solution of 1-dimethylamino-1-methoxyethylene (2.3 cc) in dimethylformamide (4 cc) is added, in the course of 55 minutes, to a solution of 2-benzhydryloxycarbonyl-7-diethoxyphosphoramido-3-methyl-8-oxo-5-thia-1-azabicyclo[4.2.0]oct-2-ene (2.58 g) in dimethylformamide (10 cc), heated to 80° C., whilst keeping the temperature at 80° C. This yields a solution of 2-benzhydryloxycarbonyl-7-diethoxyphosphoramido-3-(2-dimethylaminoprop-1-en-1-yl)-8-oxo-5-thia-1-azabicyclo[4.2.0]-oct-2-ene, which is poured into a mixture of iced water (150 cc) and ethyl acetate (100 cc). The organic phase is washed with water (250 cc), dried over sodium sulphate and filtered in the presence of decolorising charcoal and the filtrate is evaporated to dryness under reduced pressure (20 mm Hg; 2.7 kPa). The residue is chromatographed on a column of Merck silica gel (0.06–0.2) (30 g) (diameter of the column: 2.2 cm, height: 18 cm). Elution is carried out with a 50/50 (by volume) ethyl acetate/cyclohexane mixture (100 cc) and then a 70/30 (by volume) ethyl acetate/cyclohexane mixture (300 cc), 30 cc fractions being collected. Fractions 9 to 12 are combined and evaporated to dryness under reduced pressure (20 mm Hg; 2.7 kPa). This yields a 75/25 mixture of 3-acetonyl-2-benzhydryloxycarbonyl-7-diethoxyphosphoramido-8-oxo-5-thia-1- azabicyclo[4.2.0]oct-2-ene and -oct-3-ene (0.31 g) in the form of a yellow solid.

Rf=0.36 [Merck silica plate F$_{254}$, thickness 0.25 mm; eluant: 80/20 (by volume) ethyl acetate/cyclohexane].

Proton NMR spectrum (350 MHz, d$_6$-DMSO, δ in ppm, J in Hz): 1.15 to 1.30 (m, 6H, —CH$_3$ of the oct-2-ene and the oct-3-ene); 1.88 (s, —CO—CH$_3$ of the oct-3-ene); 1.96 (s, —CO—CH$_3$ of the oct-2-ene); 3.24 and 3.44 (2d, J=17.5, —CH$_2$—CO— of the oct-3-ene); 3.40 and 3.60 (2d, J=18.5, —CH$_2$—S— of the oct-2-ene); 3.53 and 3.65 (2d, J=17.5, —CH$_2$—CO— of the oct-2-ene); 3.90 to 4.05 (m, 4H, —OCH$_2$— of the oct-2-ene and the oct-3-ene); 4.97 (dt, J=11 and 4.5, —H in the 7-position of the oct-3-ene); 5.06 (d, J=4.5, —H in the 6-position of the oct-3-ene); 5.08 (d, J=4.5, —H in the 6-position of the oct-2-ene); 5.11 (s broad, —H in the 2-position of the oct-3-ene); 5.16 (dt, J=11 and 4.5, —H in the 7-position of the oct-2-ene); 6.24 (t, J=11, >N—H of the oct-2-ene); 6.27 (t, J=11, >N—H of the oct-3-ene); 6.40 (s broad, —H in the 4-position of the oct-3-ene); 6.77 (s, —COOCH(C$_6$H$_5$)$_2$ of the oct-3-ene); 6.84 (s, —COO—CH(C$_6$H$_5$)$_2$ of the oct-2-ene); 7.25 to 7.55 (m, 10H, aromatic protons of the oct-2-ene and oct-3-ene).

The following examples show how the products of the general formula (I) (if appropriate prepared in situ) can be used for the preparation of the products of the general formula (XV) or (XVII).

REFERENCE EXAMPLE 1

1-Dimethylamino-1-methoxyethylene (218 g) is added dropwise, in the course of 55 minutes, to a solution of 2-benzhydryloxycarbonyl-7-t-butoxycarbonylamino-3-methyl-8-oxo-5-thia-1-azabicyclo[4.2.0]oct-2-ene (345 g) in anhydrous dimethylformamide (1,600 cc) at 80° C. This yields a solution of 2-benzhydryloxycarbonyl-7-t-butoxycarbonylamino-3-(2-dimethylaminoprop-1-en-1-yl)-8-oxo-5-thia-1-azabicyclo[4.2.0]oct-2-ene, which is poured into a stirred mixture of distilled water (2 liters), ice (2 kg) and ethyl acetate (2.5 liters). The organic phase is decanted, washed with distilled water (3×1 liter), dried over sodium sulphate and concentrated to dryness under reduced pressure (20 mm Hg; 2.7 kPa) at 30° C. The residue is divided into 2 equal parts which are each chromatographed separately on a column of Merck silica gel (0.06–0.2) (1,500 g) (diameter of the column: 8.5 cm; height: 70 cm). Each column is eluted with a 23/77 (by volume) ethyl acetate/cyclohexane mixture (20 liters), 1 liter fractions being collected. Fractions 7 to 15 from each column are concentrated to dryness at 30° C. under reduced pressure (20 mm Hg; 2.7 kPa). This yields 3-acetonyl-2-benzhydryloxycarbonyl-7-t-butoxycarbonylamino-8-oxo-5-thia-1-azabicyclo[4.2.0]oct-2-ene (149 g) in the form of a hard yellow foam.

Infra-red spectrum (CHCl$_3$), characteristic bands (cm$^{-1}$): 3,440, 1,780, 1,720, 1,505, 1,455, 1,395, 1,370, 1,160, 695.

Proton NMR spectrum (350 MHz, CDCl$_3$, δ in ppm, J in Hz): 1.48 (s, 9H, —C(CH$_3$)$_3$); 2.10 (s, 3H, CH$_3$CO—); 3.29 and 3.62 (2d, J=19, 2H, —SCH$_2$—); 3.57 and 3.67 (2d, J=16, 2H, —CH$_2$CO—); 5.00 (d, J=4, 1H, H$_6$); 5.23 (d, J=9, 1H, —CONH—); 5.62 (dd, J=4 and 9, 1H, H$_7$); 6.97 (s, 1H, —COOCH<).

3-Acetonyl-2-benzhydryloxycarbonyl-7-t-butoxycarbonylamino-8-oxo-5-thia-1-azabicyclo[4.2.0]oct-2-ene can be used in accordance with one or other of the following methods:

A. A 1.6M solution of n-butyllithium in hexane (26.5 cc) is added, in the course of 1 minute, to a solution of 2,2,6,6-tetramethylpiperidine (6.6 g) in tetrahydrofuran (50 cc) at 20° C. The mixture is stirred for 30 minutes at 20° C. and then cooled to −70° C. A solution of 3-acetonyl-2-benzhydryloxycarbonyl-7-t-butoxycarbonylamino-8-oxo-5-thia-1-azabicyclo[4.2.0]oct-2-ene (22.2 g) in tetrahydrofuran (50 cc) is then added dropwise in the course of 20 minutes. The mixture is stirred for 30 minutes at −70° C. and hexamethylphosphorotriamide (35 cc) is added in the course of 3 minutes, followed by trifluoromethanesulphonic anhydride (10.7 cc) in the course of 5 minutes. The mixture is stirred for 45 minutes at −70° C. and then left to return to 0° C. in the course of 1 hour. It is then diluted with ethyl acetate (500 cc) and washed successively with 0.2N hydrochloric acid (650 cc) and distilled water (300 cc). The solution is dried over sodium sulphate and concentrated to dryness under reduced pressure (20 mm Hg; 2.7 kPa) at 20° C. The residue is chromatographed on a column of Merck silica gel (0.06–0.2) (300 g) (diameter of the column: 3.5 cm, height: 70 cm). Elution is carried out with a 20/80 (by volume) ethyl acetate/cyclohexane mixture (2 liters) and 100 cc fractions are collected. Fractions 3 to 9 are concentrated to dryness under reduced pressure (20 mm Hg; 2.7 kPa) at 20° C. This yields a 66/34 (mols) mixture of the Z form of 2-benzhydryloxycarbonyl-7-t-butoxycarbonylamino-8-oxo-3-(2-trifluoromethanesulphonyloxyprop-1-en-1-yl)-5-thia-1-azabicyclo[4.2.0]oct-2-ene and -oct-3-ene (6.3 g) in the form of a yellow oil.

Infra-red spectrum (CHCl$_3$), characteristic bands (cm$^{-1}$): 3,440, 1,790, 1,720, 1,505, 1,455, 1,420, 1,370, 1,155, 1,140, 910, 700.

Proton NMR spectrum (350 MHz, CDCl$_3$, δ in ppm, J in Hz): 1.47 (s, 9H, —C(CH$_3$)$_3$); 1.94 (s, 3H,

of the oct-2-ene); 1.99 (s, 3H,

of the oct-3-ene); 3.43 and 3.72 (2d, J=18, 2H, —SCH$_2$—); 5.00 (d, J=4, H$_6$ of the oct-2-ene); 5.04 (s, H$_2$ of the oct-3-ene); 5.26 (d, J=4, H$_6$ of the oct-3-ene); 5.27 (d, J=9, —CONH— of the oct-2-ene); 5.35 to 5.48 (m, 2H, H$_7$ and —CONH— of the oct-3-ene); 5.56 (s, H$_4$ of the oct-3-ene); 5.65 (dd, J=4 and 9, H$_7$ of the oct-2-ene); 6.17 (s, 1H,

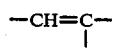

of the oct-2-ene); 6.65 (s, 1H,

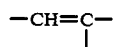

of the oct-3-ene); 6.87 (s, 1H, —COOCH< of the oct-3-ene); 6.95 (s, 1H, —COOCH< of the oct-2-ene).

A mixture of the Z form of 2-benzhydryloxycarbonyl-7-t-butoxycarbonylamino-8-oxo-3-(2-trifluoromethanesulphonyloxyprop-1-en-1-yl)-5-thia-1-azabicyclo[4.2.0]oct-2-ene and -oct-3-ene can be used in accordance with one or other of the following methods:

$A_1$. The sodium salt of 5-mercapto-2-methyl-1,3,4-thiadiazole (1.53 g) is added to a solution of a 66/34 mixture of the Z form of 2-benzhydryloxycarbonyl-7-t-butoxycarbonylamino-8-oxo-3-(2-trifluoromethanesulphonyloxyprop-1-en-1-yl)-5-thia-1-azabicyclo[4.2.0]oct-2-ene and -oct-3-ene (5.9 g) in dimethylformamide (100 cc) at 20° C. The mixture is stirred for 1 hour 10 minutes at 20° C. and the solution is then diluted with water (500 cc). Extraction is carried out with ethyl acetate (300 cc), the organic phase is dried over sodium sulphate and concentrated to dryness at 20° C. under reduced pressure (20 mm Hg; 2.7 kPa) and the residue is chromatographed on a column of Merck silica gel (0.06–0.2) (100 g) (diameter of the column: 3.5 cm; height: 25 cm). Elution is carried out with a 35/65 (by volume) ethyl acetate/cyclohexane mixture (1 liter) and 60 cc fractions are collected. Fractions 8 to 14 are concentrated to dryness at 20° C. under reduced pressure (20 mm Hg; 2.7 kPa). This yields a 40/60 mixture of the Z form of 2-benzhydryloxycarbonyl-7-t-butoxycarbonylamino-3-{2-[(2-methyl-1,3,4-thiadiazol-5-yl)-thio]-prop-1-en-1-yl}-8-oxo-5-thia-1-azabicyclo[4.2.0]oct-2-ene and -oct-3-ene (1.35 g) in the form of a hard yellow foam.

Infra-red spectrum (CHCl₃), characteristic bands (cm⁻¹): 3,440, 1,780, 1,720, 1,505, 1,455, 1,390, 1,370, 1,160.

Proton NMR spectrum (350 MHz, CDCl₃, δ in ppm, J in Hz): 1.48 (s, 9H, —C(CH₃)₃); 2.06 (s broad,

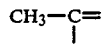

of the oct-2-ene and oct-3-ene); 2.74 (s, CH₃—Het of the oct-2-ene); 2.76 (s, CH₃—Het of the oct-3-ene); 3.66 and 3.76 (2d, J=18, —SCH₂— of the oct-3-ene); 5.04 (d, J=4, H₆ of the oct-2-ene); 5.19 (s, H₂ of the oct-3-ene); 5.25 (d, J=4, H₆ of the oct-3-ene); 5.31 (d, J=8, —CONH— of the oct-2-ene); 5.36 to 5.46 (m, H₇ and —CONH— of the oct-3-ene); 5.66 (dd, J=4 and 8, H₇ of the oct-2-ene); 6.18 (s, H₄ of the oct-3-ene); 6.58 (s,

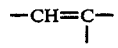

of the oct-3-ene); 6.64 (s,

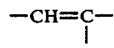

of the oct-2-ene); 6.90 (s, —COOCH< of the oct-3-ene); 6.97 (s, —COOCH< of the oct-2-ene).

A solution of the Z form of 2-benzhydryloxycarbonyl-7-t-butoxycarbonylamino-3-{2-[(2-methyl-1,3,4-thiadiazol-5-yl)-thio]-prop-1-en-1-yl}-8-oxo-5-thia-1-azabicyclo[4.2.0]oct-2-ene and -oct-3-ene (0.22 g) in methylene chloride (10 cc) is cooled to 0° C. A solution of 85% pure m-chloroperbenzoic acid (0.07 g) in methylene chloride (5 cc) is added dropwise in the course of 20 minutes. The solution is then stirred for 5 minutes at 0° C., washed with a saturated solution of sodium bicarbonate (20 cc), dried over sodium sulphate and concentrated to dryness under reduced pressure (20 mm Hg; 2.7 kPa) at 20° C. The residue is chromatographed on a column of Merck silica gel (0.06–0.2) (4 g) (diameter of the column: 1 cm; height: 10 cm). Elution is carried out with a 60/40 (by volume) ethyl acetate/cyclohexane mixture (100 cc) and and 3 cc fractions are collected. Fractions 11 to 22 are concentrated to dryness under reduced pressure (20 mm Hg; 2.7 kPa) at 20° C. This yields the Z form of 2-benzhydryloxycarbonyl-7-t-butoxycarbonylamino-3-{2-[(2-methyl-1,3,4-thiadiazol-5-yl)-thio]-prop-1-en-1-yl}-8-oxo-5-thia-1-azabicyclo[4.2.0]oct-2-ene-5-oxide (0.12 g) in the form of a hard white foam.

Infra-red spectrum (CHCl₃), characteristic bands (cm⁻¹): 3,420, 1,800, 1,720, 1,505, 1,455, 1,370, 1,160, 1,045, 695.

Proton NMR spectrum (350 MHz, CDCl₃, δ in ppm, J in Hz): 1.48 (s, 9H, —C(CH₃)₃); 2.05 (s, 3H, —CH₃); 2.72 (s, 3H, CH₃—heterocycle); 3.70 and 4.03 (2d, J=18, 2H, —SCH₂—); 4.58 (d, J=4, 1H, H₆); 5.77 (d, J=8, 1H, —CONH—); 5.85 (dd, J=4 and 9, 1H, H₇); 6.75 (s, 1H, —CH=); 6.98 (s, —COOCH<).

A solution of the Z form of 2-benzhydryloxycarbonyl-7-t-butoxycarbonylamino-3-{2-[(2-methyl-1,3,4-thiadiazol-5-yl)-thio]-prop-1-en-1-yl}-8-oxo-5-thia-1-azabicyclo[4.2.0]oct-2-ene-5-oxide (4.45 g) in acetonitrile (150 cc) is heated to 40° C. A solution of p-toluenesulphonic acid (monohydrate) (2.59 g) in acetonitrile (75 cc) is added dropwise in the course of 5 minutes. The mixture is stirred at 40° C. for 35 minutes and then poured into a saturated aqueous solution of sodium bicarbonate (200 cc). Distilled water (500 cc) is added and extraction is carried out with methylene chloride (500 cc). The organic phase is washed with distilled water (500 cc), dried over magnesium sulphate and concentrated to dryness under reduced pressure (20 mm Hg; 2.7 kPa) at 20° C. This yields the Z form of 7-amino-2-benzhydryloxycarbonyl-3-{2-[(2-methyl-1,3,4-thiadiazol-5-yl)-thio]-prop-1-en-1-yl}-8-oxo-5-thia-1-azabicyclo[4.2.0]oct-2-ene-5-oxide (3.53 g) in the form of a hard brown foam.

Infra-red spectrum (CHCl₃), characteristic bands (cm⁻¹): 3,420, 1,800, 1,725, 1,500, 1,455, 1,370, 1,160, 1,050, 695.

A solution of the Z form of 7-amino-2-benzhydryloxycarbonyl-3-{2-[(2-methyl-1,3,4-thiadiazol-5-yl)-thio]-prop-1-en-1-yl}-8-oxo-5-thia-1-azabicyclo[4.2.0]oct-2-ene-5-oxide (3.53 g) in methylene chloride (250 cc) is cooled to 4° C. 2-Methoxyimino-2-(2-tritylaminothiazol-4-yl)acetic acid (3.28 g) and dicyclohexylcarbodiimide (1.54 g) are added successively. The mixture is stirred for 1½ hours at 4° C. and then concentrated to dryness under reduced pressure (20 mm Hg; 2.7 kPa) at 20° C. The residue is taken up in ethyl acetate (50 cc) and the insoluble material is filtered off. The solution is washed with a saturated aqueous solution of sodium bicarbonate (100 cc) and then with 0.1N hydrochloric acid (100 cc). It is dried over sodium sulphate and concentrated to dryness under reduced pressure (20 mm Hg; 2.7 kPa) at 20° C. The residue is chromatographed on a column of Merck silica gel (0.06–0.2) (80 g) (diameter of the column: 3 cm; height: 64 cm). Elution is carried out with a 35/65 (by volume) ethyl acetate/cyclohexane mixture (300 cc) and then with a 70/30 (by volume) ethyl acetate/cyclohexane mixture (1,200 cc), 60 cc fractions being collected. Fractions 12 to 20 are concentrated to dryness under reduced pressure (20 mm Hg; 2.7 kPa) at 20° C. This yields the Z form of the syn isomer of 2-benzhydryloxycarbonyl-3-{2-[(2-methyl-1,3,4-thiadiazol-5-yl)-thio]-prop-1-en-1-yl}-7-[2-methoxyimino-2-(2-tritylaminothiazol-4-yl)-acetamido]-8-oxo-5-thia-1-azabicyclo[4.2.0]oct-2-ene-5-oxide (2 g) in the form of a hard white foam.

Infra-red spectrum (KBr), characteristic bands (cm$^{-1}$): 3,420, 1,800, 1,730, 1,685, 1,530, 1,495, 1,450, 1,040, 755, 705.

Proton NMR spectrum (350 MHz, CDCl$_3$, δ in ppm, J in Hz): 2.05 (s, 3H, CH$_3$—C=); 2.72 (s, 3H, CH$_3$—heterocycle); 3.71 and 4.06 (2d, J=18, 2H, —SCH$_2$—); 4.12 (s, 3H, =NOCH$_3$); 4.61 (d, J=5, 1H, H$_6$); 6.21 (dd, J=5 and 9, 1H, H$_7$); 6.73 (s, 1H, —CH=); 6.76 (s, 1H, H on the thiazole); 6.97 (s, 1H, —COOCH<); 7.14 (s broad, 1H, —NH—trityl); 7.44 (d, J=9, 1H, —CONH—).

A solution of the Z form of the syn isomer of 2-benzhydryloxycarbonyl-3-{2-[(2-methyl-1,3,4-thiadiazol-5-yl)-thio]-prop-1-en-1-yl}-7-[2-methoxyimino-2-(2-tritylaminothiazol-4-yl)-acetamido]-8-oxo-5-thia-1-azabicyclo[4.2.0]oct-2-ene-5-oxide (2.52 g) in methylene chloride (40 cc) is cooled to −10° C. N,N-Dimethylacetamide (0.95 cc) and phosphorus trichloride (0.7 g) are added successively. The solution is stirred for 20 minutes at −10° C. and then poured into a saturated aqueous solution of sodium bicarbonate (50 cc). It is diluted with distilled water (200 cc) and extraction is carried out with ethyl acetate (300 cc). The organic phase is dried over sodium sulphate and concentrated to dryness under reduced pressure (20 mm Hg; 2.7 kPa) at 20° C. The residue is chromatographed on a column of Merck silica gel (0.06–0.20) (25 g) (diameter of the column: 2 cm; height: 15 cm). Elution is carried out with a 50/50 (by volume) ethyl acetate/cyclohexane mixture (500 cc), 30 cc fractions being collected. Fractions 4 to 13 are concentrated to dryness under reduced pressure (20 mm Hg; 2.7 kPa) at 20° C. This yields the Z form of the syn isomer of 2-benzhydryloxycarbonyl-3-{2-[(2-methyl-1,3,4-thiadiazol-5-yl)-thio]-prop-1-en-1-yl}-7-[2-methoxyimino-2-(2-tritylaminothiazol-4-yl)-acetamido]-8-oxo-5-thia-1-azabicyclo[4.2.0]oct-2-ene (0.77 g) in the form of a hard white foam.

Infra-red spectrum (KBr), characteristic bands (cm$^{-1}$): 1,790, 1,725, 1,685, 1,525, 1,495, 1,450, 1,050, 750, 700.

Proton NMR spectrum (350 MHz, CDCl$_3$, δ in ppm, J in Hz): 2.02 (s, 3H,

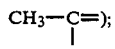
CH$_3$—C=);

2.7 (s, 3H, CH$_3$—heterocycle); 3.63 and 3.74 (2d, J=18, 2H, —SCH$_2$—); 4.07 (s, 3H, =NOCH$_3$); 5.09 (d, J=4, 1H, H$_6$); 5.94 (dd, J=4 and 9, 1H, H$_7$); 6.6 (s, 1H, —CH=); 6.76 (s, 1H, H of the thiazole); 6.84 (d, J=9, 1H, —CONH—); 6.94 (s, 1H, —COOCH<); 7.04 (s broad, 1H, —NH—trityl).

The Z form of the syn isomer of 2-benzhydryloxycarbonyl-3-{2-[(2-methyl-1,3,4-thiadiazol-5-yl)-thio]-prop-1-en-1-yl}-7-[2-methoxyimino-2-(2-tritylaminothiazol-4-yl)-acetamido]-8-oxo-5-thia-1-azabicyclo[4.2.0]oct-2-ene (0.76 g) is dissolved in formic acid (8 cc). The solution is heated to 50° C. and distilled water (4 cc) is added dropwise in the course of 10 minutes. The mixture is stirred for 30 minutes at 50° C., distilled water (4 cc) is then added, the mixture is cooled and filtered and the solution is concentrated to dryness under reduced pressure (1 mm Hg; 0.13 kPa) at 40° C. Ethanol (40 cc) is added and evaporated off under reduced pressure (1 mm Hg; 0.13 kPa) at 30° C., and this operation is repeated a further 2 times. The residue is taken up in ethanol (10 cc), the solution is filtered, the cake is washed with diethyl ether (20 cc), the filtrate is dried over sodium sulphate and the solvent is evaporated off under reduced pressure (1 mm Hg; 0.13 kPa) at 20° C. The Z form of the syn isomer of 7-[2-(2-aminothiazol-4-yl)-2-methoxyiminoacetamido]-2-carboxy-3-{2-[(2-methyl-1,3,4-thiadiazol-5-yl)-thio]-prop-1-en-1-yl}-8-oxo-5-thia-1-azabicyclo[4.2.0]oct-2-ene (60 mg) is thus isolated in the form of a yellow powder.

Infra-red spectrum (KBr), characteristic bands (cm$^{-1}$): 3,600, 2,700, 1,765, 1,670, 1,625, 1,535, 1,365, 1,035.

Proton NMR spectrum (350 MHz, d$_6$-DMSO, δ in ppm, J in Hz): 2.24 (s broad,

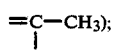
=C—CH$_3$);

2.75 (s, —CH$_3$ of the thiadiazole); 3.87 (s, =N—OCH$_3$); 4.51 (d, J=14, 1H of the —H atoms of the —S—CH$_2$—); 5.44 (dd, J=5 and 9, —H in the 7-position); 5.62 (d, J=5, —H in the 6-position); 6.75 (s, —H of the thiazole); 7.07 (s, —CH=); 7.20 (s broad, —NH$_2$); 9.55 (d, J=9, —CO—NH—).

A$_2$. A solution of 85% pure m-chloroperbenzoic acid (0.13 g) in methylene chloride (5 cc) is added, in the course of 20 minutes, to a solution of the Z form of 2-benzhydryloxycarbonyl-7-t-butoxycarbonylamino-8-oxo-3-(2-trifluoromethanesulphonyloxyprop-1-en-1-yl)-5-thia-1-azabicyclo[4.2.0]oct-2-ene and -oct-3-ene (0.42 g) in methylene chloride (10 cc) at 0° C. The mixture is stirred at 20° C. for 10 hours and the solution is then washed with a saturated solution of sodium bicarbonate (20 cc) and dried over sodium sulphate. It is concentrated to dryness under reduced pressure (20 mm Hg; 2.7 kPa) at 20° C. and the residue is chromatographed on a column of Merck silica gel (0.06–0.20) (6 g) (diameter of the column; 1 cm; height: 12 cm). Elution is carried out with a 30/70 (by volume) ethyl acetate/cyclohexane mixture (100 cc), 3 cc fractions being collected. Fractions 8 to 18 are concentrated to dryness under reduced pressure (20 mm Hg; 2.7 kPa) at 20° C. This yields 2-benzhydryloxycarbonyl-7-t-butoxycarbonylamino-8-oxo-3-(2-trifluoromethanesulphonyloxyprop-1-en-1-yl)-5-thia-1-azabicyclo[4.2.0]oct-2-ene 5-oxide (0.14 g) in the form of a hard white foam.

Infra-red spectrum (CHBr$_3$), characteristic bands (cm$^{-1}$): 3,420, 1,810, 1,720, 1,505, 1,455, 1,420, 1,220, 1,040.

Proton NMR spectrum (350 MHz, CDCl$_3$, δ in ppm, J in Hz): 1.50 (s, 9H, —C(CH$_3$)$_3$); 1.98 (s, 3H,

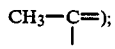
CH$_3$—C=);

3.52 and 3.82 (2d, J=18, 2H, —SCH$_2$—); 4.59 (d, J=4, 1H, H$_6$); 5.73 (d, J=8, 1H, —CONH—); 5.86 (dd, J=4 and 8, 1H, H$_7$); 6.44 (s, 1H, —CH=); 6.98 (s, 1H, —COOCH<).

B. A 1.6M solution of n-butyllithium in hexane (5.37 cc) is added, in the course of 2 minutes, to a solution of 2,2,6,6-tetramethylpiperidine (1.28 g) in tetrahydrofuran (10 cc) at 20° C. The mixture is stirred for 1 hour at 20° C . and then cooled to −70° C. A solution of 3-acetonyl-2-benzhydryloxycarbonyl-7-t-butoxycarbonylamino-8-oxo-5-thia-1-azabicyclo[4.2.0]oct-2-ene (4.5 g) in tetrahydrofuran (10 cc) is then added dropwise in the courese of 20 minutes and the solution is then stirred for 30 minutes at −70° C. Hexamethylphosphorotriamide (7 cc) is then added in the course of 3 minutes, followed by trifluoromethanesulphonic anhydride (4.34 cc) in the course of 3 minutes. The mixture is stirred for a further 40 minutes at −70° C. and then left to return to 0° C. in the courese of 40 minutes. It is then poured into a stirred mixture of 0.25N hydrochloric acid (125 cc) and ethyl acetate (50 cc). The organic phase is decanted, washed with a saturated aqueous solution of sodium bicarbonate (50 cc), dried over sodium sulphate and concentrated to dryness under reduced pressure (20 mm Hg; 2.7 kPa) at 20° C. The residue is chromatographed on a column of Merck silica gel (0.06–0.20) (90 g) (diameter of the column: 2.4 cm; height: 45 cm). Elution is carried out with a 20/80 (by volume) ethyl acetate/cyclohexane mixture (1 liter) and 100 cc fractions are collected. Fractions 2 to 7 are concentrated to dryness under reduced pressure (20 mm Hg; 2.7 kPa) at 20° C. This yields the Z form of 2-benzhydryloxycarbonyl-7-t-butoxycarbonylamino-8-oxo-3-(2-trifluoromethanesulphonyloxyprop-1-en-1-yl)-5-thia-1-azabicyclo[4.2.0]oct-2-ene (2 g) in the form of a hard yellow foam.

Infra-red spectrum (CHCl₃), characteristic bands (cm⁻¹): 3,440, 1,790, 1,720, 1,505, 1,455, 1,420, 1,370, 1,155, 1,140, 910, 700.

Proton NMR spectrum (350 MHz, CDCl₃, δ in ppm, J in Hz): 1.47 (s, 9H, —C(CH₃)₃); 1.94 (s, 3H,

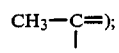

3.43 and 3.72 (2d, J=18, 2H, —SCH₂—); 5.00 (d, J=4, H₆); 5.27 (d, J=9, —CONH—); 5.65 (dd, J=4 and 9, H₇); 6.17 (s, 1H,

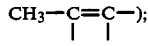

6.95 (s, 1H, —COOCH<).

C. A 1.6M solution of butyllithium in hexane (3.44 cc) is added, in the course of 10 minutes, to a solution of 2,2,6,6-tetramethylpiperidine (0.78 g) in tetrahydrofuran (5 cc) at 20° C. The solution is stirred for 10 minutes at 20° C. and then cooled to −70° C. A solution of 3-acetonyl-2-benzhydryloxycarbonyl-7-t-butoxycarbonylamino-8-oxo-5-thia-1-azabicyclo[4.2.0]oct-2-ene (2.54 g) in tetrahydrofuran (6 cc) is then added in the course of 20 minutes, and the mixture is then stirred for 15 minutes at −70° C. Hexamethylphosphorotriamide (7 cc) is added in the course of 3 minutes, followed by a solution of p-toluenesulphonyl chloride (5.23 g) in tetrahydrofuran (7 cc) in the course of 3 minutes. The mixture is stirred for 45 minutes at −70° C., the temperature is then left to rise to 0° C. and the solution is diluted with ethyl acetate (100 cc) and washed successively with a 0.1N solution of citric acid (50 cc), a saturated aqueous solution of sodium bicarbonate (50 cc) and distilled water (100 cc). The organic phase is dried over sodium sulphate and concentrated to dryness under reduced pressure (20 mm Hg; 2.7 kPa) at 20° C. The residue is chromatographed on a column of Merck silica gel (0.06–0.20) (110 g) (diameter of the column: 3 cm; height: 26 cm). Elution is carried out with a 15/80 (by volume) ethyl acetate/cyclohexane mixture (1,200 cc), 60 cc fractions being collected. Fractions 3 to 15 are concentrated to dryness under reduced pressure (20 mm Hg; 2.7 kPa) at 20° C. This yields the Z form of 2-benzhydryloxycarbonyl-7-t-butoxycarbonylamino-3-(2-tosyloxyprop-1-en-1-yl)-8-oxo-5-thia-1-azabicyclo[4.2.0]oct-2-ene (0.94 g) in the form of a hard, pale yellow foam.

Infra-red spectrum (CHBr₃), characteristic bands (cm⁻¹): 3,420, 1,785, 1,720, 1,595, 1,500, 1,455, 1,370, 815, 530.

Proton NMR spectrum (350 MHz, CDCl₃, δ in ppm, J in Hz): 1.5 (s, 9H, —C(CH₃)₃); 2.0 (s, 3H,

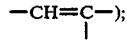

2.35 (s, 3H, —CH₃ of the tosyl); 3.51 (s broad, 2H, —SCH₂—); 4.78 (d, J=4, 1H, H₆); 5.92 (dd, J=4 and 9, 1H, H₇); 6.08 (s, 1H, —CH=); 6.93 (s, 1H, —COOCH<).

D. A 1.6M solution of butyllithium in hexane (10.3 cc) is added, in the course of 10 minutes, to a solution of 2,2,6,6-tetramethylpiperidine (2.33 g) in tetrahydrofuran (15 cc) at 20° C. The mixture is stirred for 20 minutes at 20° C. and then cooled to −70° C. A solution of 3-acetonyl-2-benzhydryloxycarbonyl-7-t-butoxycarbonylamino-8-oxo-5-thia-1-azabicyclo[4.2.0]oct-2-ene (7.61 g) in tetrahydrofuran (20 cc) is then added in the course of 15 minutes. The mixture is stirred for a further 20 minutes at −70° C. and hexamethylphosphorotriamide (15 cc) is then added in the course of 3 minutes, followed by a solution of methanesulphonyl chloride (4.5 cc) in tetrahydrofuran (10 cc) in the course of 3 minutes. The mixture is stirred for 45 minutes at −70° C., the temperature is then left to rise to 0° C. and the mixture is diluted with ethyl acetate (300 cc). The solution is washed successively with a saturated solution of sodium bicarbonate (100 cc) and distilled water (100 cc), dried over sodium sulphate and concentrated to dryness under reduced pressure (20 mm Hg; 2.7 kPa) at 20° C. The residue is chromatographed on a column of Merck silica gel (0.06–0.20) (150 g) (diameter of the column: 3.7 cm; height: 30 cm). Elution is carried out with a 22/78 (by volume) ethyl acetate/cyclohexane mixture (2.5 liters), 100 cc fractions being collected. Fractions 12 to 20 are concentrated to dryness under reduced pressure (20 mm Hg; 2.7 kPa) at 20° C. This yields the Z form of 2-benzhydryloxycarbonyl-7-t-butoxycarbonylamino-3-(2-mesyloxy-prop-1-en-1-yl)-8-oxo-5-thia-1-azabicyclo[4.2.0]oct-2-ene (3.2 g) in the form of a hard, pale yellow foam.

Infra-red spectrum (CHCl₃), characteristic bands (cm⁻¹): 3,430, 1,790, 1,720, 1,610, 1,500, 1,455, 1,375, 1,155, 970.

Proton NMR spectrum (350 MHz, CDCl₃, δ in ppm, J in Hz): 1.50 (s, 9H, —C(CH₃)₃); 1.80 (s, 3H,

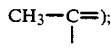

3.15 (s, 3H, —OSO$_2$CH$_3$); 3.43 and 3.77 (2d, J=18, 2H, —SCH$_2$—); 5.06 (s, J=4, 1H, H$_6$); 5.38 (d, J=9, 1H, —CONH—); 5.74 (dd, J=4 and 9, 1H, H$_7$); 6.97 (s, 1H, —COOCH<).

A solution of the Z form of 2-benzhydryloxycarbonyl-7-t-butoxycarbonylamino-3-(2-mesyloxyprop-1-en-1-yl)-8-oxo-5-thia-1-azabicyclo[4.2.0]oct-2-ene (1 g) in acetonitrile (12 cc) is heated to 38° C. A solution of p-toluenesulphonic acid monohydrate (0.63 g) in acetonitrile (10 cc) is added in the course of 20 minutes and the mixture is then kept at 38° C. for 1 hour. It is diluted with methylene chloride (30 cc) and the solution obtained is washed with a saturated solution of sodium bicarbonate (20 cc) and then with distilled water (50 cc), dried over sodium sulphate and concentrated to a volume of 15 cc under reduced pressure (20 mm Hg; 2.7 kPa) at 20° C. This yields a solution of the Z form of 7-amino-2-benzhydryloxycarbonyl-3-(2-mesyloxyprop-1-en-1-yl)-8-oxo-5-thia-1-azabicyclo[4.2.0]oct-2-ene, to which triethylamine (0.7 cc) is added (Solution A).

N,N-Dimethylacetamide (0.16 cc) and a solution of phosgene in benzene (2.5M) (0.81 cc) are added successively, in the course of 20 minutes, to a suspension of the syn isomer of 2-methoxyimino-2-(2-tritylaminothiazol-4-yl)-acetic acid (0.8 g) in methylene chloride (12 cc), cooled to −10° C. The mixture is stirred for a further 16 hours at −10° C. and solution A is then added dropwise in the course of 25 minutes. The solution is stirred for 2 hours at −10° C. and then diluted with ethyl acetate (50 cc) and washed with 0.1N hydrochloric acid (50 cc), a saturated solution of sodium bicarbonate (50 cc) and then distilled water (50 cc). It is dried over sodium sulphate and concentrated to dryness under reduced pressure (20 mm Hg; 2.7 kPa) at 20° C. The residue is chromatographed on a column of Merck silica gel (0.06-0.2) (10 g) (diameter of the column: 1.5 cm; height: 12 cm). Elution is carried out with a 25/75 (by volume) ethyl acetate/cyclohexane mixture (700 cc), 25 cc fractions being collected. Fractions 10 to 21 are concentrated to dryness under reduced pressure (20 mm Hg; 2.7 kPa) at 20° C. This yields the E form of the syn isomer of 2-benzhydryloxycarbonyl-3-(2-mesyloxyprop-1-en-1-yl)-7-[2-methoxyimino-2-(2-tritylaminothiazol-4-yl)-acetamido]-8-oxo-5-thia-1-azabicyclo[4.2.0]oct-2-ene (0.43 g) in the form of a hard yellow foam.

Proton NMR spectrum (350 MHz, CDCl$_3$, δ in ppm, J in Hz): 1.8 (s,

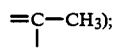

3.18 (s, —OSO$_2$—CH$_3$); 3.42 and 3.78 (2d, J=18, —S—CH$_2$—); 4.08 (s, =N—OCH$_3$); 5.13 (d, J=5, —H in the 6-position); 6.09 (dd, J=5 and 9, —H in the 7-position); 6.86 (d, J=9, —CO—NH—); 6.95 (s, —COO—CH(C$_6$H$_5$)$_2$); 7.05 (m, —NH—C(C$_6$H$_5$)$_3$); 7.2 to 7.5 (m, aromatic protons).

The products obtained under A$_2$, B, C and D can be used for preparing a product of the general formula (XVII) by analogy with the method described under A$_1$.

REFERENCE EXAMPLE 2

A solution of p-toluenesulphonic acid monohydrate (15.2 g) in acetonitrile (200 cc) is added, in the course of 20 minutes, to a solution of 3-acetonyl-2-benzhydryloxycarbonyl-7-t-butoxycarbonylamino-8-oxo-5-thia-1-azabicyclo[4.2.0]oct-2-ene (20.9 g) in acetonitrile (400 cc) at 38° C. The mixture is kept at 40° C. for 25 minutes and then concentrated to dryness under reduced pressure (20 mm Hg; 2.7 kPa) at 40° C. The residue is taken up in ethyl acetate (500 cc), distilled water (500 cc) and a saturated aqueous solution of sodium bicarbonate (150 cc). The organic phase is separated off by decantation, washed with distilled water (200 cc), dried over sodium sulphate and then concentrated to dryness under reduced pressure (20 mm Hg; 2.7 kPa) at 30° C. This yields 3-acetonyl-7-amino-2-benzhydryloxycarbonyl-8-oxo-5-thia-1-azabicyclo[4.2.0]oct-2-ene (12.5 g) in the form of an orange oil.

Infra-red spectrum (CHCl$_3$), characteristic bands (cm$^{-1}$): 3,430, 1,770, 1,720, 1,495, 1,450, 1,245, 755, 740.

Proton NMR spectrum (350 MHz, CDCl$_3$, δ in ppm, J in Hz): 2.02 (s, 3H, —CH$_3$); 3.25 and 3.50 (2d, J=18, 2H, —SCH$_2$—); 3.55 and 3.66 (2d, J=17, 2H, —CH$_2$—); 4.74 (d, J=4, 1H, H$_7$); 4.96 (d, J=4, 1H, H$_6$); 6.86 (s, 1H, —COOCH<).

3-Acetonyl-7-amino-2-benzhydryloxycarbonyl-8-oxo-5-thia-1-azabicyclo[4.2.0]oct-2-ene can be used in accordance with one or other of the following methods:

A. The syn isomer of 2-methoxyimino-2-(2-tritylaminothiazol-4-yl)-acetic acid (12 g), 4-dimethylaminopyridine (30 mg) and dicyclohexylcarbodiimide (6.72 g) are added successively to a solution of 3-acetonyl-7-amino-2-benzhydryloxycarbonyl-8-oxo-5-thia-1-azabicyclo[4.2.0]oct-2-ene (11.5 g) in methylene chloride (115 cc) at 20° C. The mixture is stirred for 3 hours at 20° C. and then concentrated to dryness under reduced pressure (20 mm Hg; 2.7 kPa) at 20° C. The residue is taken up in ethyl acetate (300 cc) and the insoluble material is removed by filtration. The solution is washed with distilled water (100 cc) and then with a saturated solution of sodium bicarbonate (50 cc). It is dried over sodium sulphate and concentrated to dryness under reduced pressure (20 mm Hg; 2.7 kPa) at 30° C. The residue is chromatographed on a column of Merck silica gel (0.06-0.20) (250 g) (diameter of the column: 4.5 cm; height: 32 cm). Elution is carried out with a 40/60 (by volume) ethyl acetate/cyclohexane mixture (3 liters), 200 cc fractions being collected. Fractions 9 to 11 are concentrated to dryness under reduced pressure (20 mm Hg; 2.7 kPa) at 20° C. This yields an 80/20 mixture of the syn isomer of the 3-acetonyl-2-benzhydryloxycarbonyl-7-[2-methoxyimino-2-(2-tritylaminothiazol-4-yl)-acetamido]-8-oxo-5-thia-1-azabicyclo[4.2.0]oct-2-ene and -oct-3-ene isomers (7 g) in the form of a hard beige foam.

Infra-red spectrum (CHCl$_3$), characteristic bands (cm$^{-1}$): 3,410, 1,785, 1,725, 1,685, 1,595, 1,585, 1,495, 1,450, 695.

Proton NMR spectrum (350 MHz, CDCl$_3$, δ in ppm, J in Hz): 2.06 (s, CH$_3$CO— of the oct-3-ene); 2.09 (s, CH$_3$CO— of the oct-2-ene); 3.30 and 3.52 (2d, J=18, —SCH$_2$—); 3.6 (s broad, —CH$_2$CO— of the oct-2-ene and of the oct-3-ene); 4.07 (s, CH$_3$ON= of the oct-3-ene); 4.08 (s, CH$_3$ON= of the oct-2-ene); 5.10 (d, J=4, H$_6$ of the oct-2-ene); 5.15 (s, H$_2$ of the oct-3-ene); 5.30 (d, J=4, H$_6$ of the oct-3-ene); 5.75 (dd, J=4 and 9, H$_7$ of the oct-3-ene); 5.95 (dd, J=4 and 9, H$_7$ of the oct-2-ene); 6.74 (s, H of the thiazole of the oct-3-ene); 6.77 (s, H of the thiazole of the oct-2-ene); 6.83 (d, J=9, —CONH— of the oct-2-ene); 6.84 (s, —COOCH< of the oct-3-ene); 6.87 (s, —COOCH< of the oct-2-ene); 6.88 (d, J=4, —CONH— of the oct-3-ene); 7.01 (s broad, —NH—trityl of the oct-2-ene and oct-3-ene).

A solution of 85% pure m-chloroperbenzoic acid (1.6 g) in methylene chloride (50 cc) is added, in the course of 20 minutes, to a solution, cooled to 0° C., of a mixture of the 3-acetonyl-2-benzhydryloxycarbonyl-7-[2-methoxyimino-2-(2-tritylaminothiazol-4-yl)-acetamido]-8-oxo-5-thia-1-azabicyclo[4.2.0]oct-2-ene and -oct-3-ene isomers (6.7 g) in methylene chloride (100 cc). The mixture is stirred for 1½ hours at 0° C. and a saturated solution of sodium bicarbonate (50 cc) is then added. The organic phase is decanted, dried over sodium sulphate and concentrated to dryness under reduced pressure (20 mm Hg; 2.7 kPa) at 20° C. The residue is chromatographed on a column of Merck silica gel (0.06–0.20) (75 g) (diameter of the column: 3 cm; height: 21 cm). Elution is carried out with a 70/30 (by volumne) ethyl acetate/cyclohexane mixture (1.5 liters), 100 cc fractions being collected. Fractions 7 to 10 are concentrated to dryness under reduced pressure (20 mm Hg; 2.7 kPa) at 20° C. This yields the syn isomer of 3-acetonyl-2-benzhydryloxycarbonyl-7-[2-methoxyimino-2-(2-tritylaminothiazol-4-yl)-acetamido]-8-oxo-5-thia-1-azabicyclo[4.2.0]oct-2-ene-5-oxide (5 g) in the form of a hard yellow foam.

A solution of 3-acetonyl-2-benzhydryloxycarbonyl-7-[2-methoxyimino-2-(2-tritylaminothiazol-4-yl)-acetamido]-8-oxo-5-thia-1-azabicyclo[4.2.0]oct-2-ene-5-oxide (5 g) in a mixture of methylene chloride (60 cc) and N,N-dimethylacetamide (2.3 cc) is cooled to −10° C. Phosphorus trichloride (1.01 cc) is then added and the mixture is stirred for one hour at −10° C. The reaction mixture is diluted with ethyl acetate (300 cc), washed successively with a saturated solution of sodium bicarbonate (50 cc) and distilled water (300 cc), dried over sodium sulphate and concentrated to dryness under reduced pressure (20 mm Hg; 2.7 kPa) at 20° C. This yields the syn isomer of 3-acetonyl-2-benzhydryloxycarbonyl-7-[2-methoxyimino-2-(2-tritylaminothiazol-4-yl)-acetamido]-8-oxo-5-thia-1-azabicyclo[4.2.0]oct-2-ene (4.5 g) in the form of a hard yellow foam.

Infra-red spectrum (CHCl₃), characteristic bands (cm⁻¹): 3,410, 1,785, 1,725, 1,685, 1,515, 1,450, 1,370, 1,040, 695.

Proton NMR spectrum (350 MHz, CDCl₃, δ in ppm, J in Hz): 2.09 (s, 3H, CH₃CO—); 3.30 and 3.52 (2d, J=18, 2H, —SCH₂—); 3.62 (s, 2H, —CH₂CO—); 4.08 (s, 3H, =NOCH₃); 5.10 (d, J=4, H₆); 5.95 (dd, J=4 and 9, H₇); 6.77 (s, H of the thiazole); 6.83 (d, J=9, —CONH—); 6.87 (s, —COOCH<); 7.01 (s, —NH—trityl).

B. A 2.5M solution of phosgene in benzene (6.47 cc) is added, in the course of 20 minutes, to a suspension of 2-methoxyimino-2-(2-tritylaminothiazol-4-yl)-acetic acid (syn isomer) (5.84 g) in a mixture of methylene chloride (50 cc) and N,N-dimethylacetamide (1.23 cc) at −10° C. The reaction is left to proceed for 16 hours at −10° C. and a solution of 3-acetonyl-7-amino-2-benzhydryloxycarbonyl-8-oxo-5-thia-1-azabicyclo[4.2.0]oct-2-ene (5.57 g) in a mixture of methylene chloride (50 cc) and triethylamine (5.6 cc) is then added in the course of 20 minutes. The mixture is stirred for 2 hours at −10° C. 0.5N hydrochloric acid (100 cc) is added and the organic phase is separated off by decantation. It is dried over sodium sulphate and concentrated to dryness under reduced pressure (20 mm Hg; 2.7 kPa) at 20° C. The residue is chromatographed on a column of Merck silica gel (0.06–0.2) (130 g) (diameter of the column: 3 cm; height: 37 cm). Elution is carried out with a 40/60 (by volume) ethyl acetate/cyclohexane mixture (2 liters), 100 cc fractions being collected. Fractions 8 to 14 are concentrated to dryness under reduced pressure (20 mm Hg; 2.7 kPa) at 20° C. This yields the syn isomer of 3-acetonyl-2-benzhydryloxycarbonyl-7-[2-methoxyimino-2-(2-tritylaminothiazol-4-yl)-acetamido]-8-oxo-5-thia-1-azabicyclo[4.2.0]oct-2-ene (4 g), which is identical to the product prepared above under A.

A solution of the syn isomer of 3-acetonyl-2-benzhydryloxycarbonyl-7-[2-methoxyimino-2-(2-tritylaminothiazol-4-yl)-acetamido]-8-oxo-5-thia-1-azabicyclo[4.2.0]oct-2-ene (4.5 g) in formic acid (42 cc) is heated to 50° C. Distilled water (15 cc) is added in the course of 15 minutes and the mixture is stirred for 15 minutes at 50° C. It is filtered and the filtrate is concentrated to dryness under reduced pressure (1 mm Hg; 0.13 kPa) at 20° C. The residue is taken up 3 times in succession with ethanol (50 cc), which is evaporated off to dryness each time under reduced pressure (1 mm Hg; 0.13 kPa) at 20° C. The solid residue is recrystallised from propan-2-ol (60 cc) and the crystals are filtered off, washed with diethyl ether (20 cc) and dried under reduced pressure (1 mm Hg; 0.13 kPa) at 30° C. This yields the syn isomer of 3-acetonyl-7-[2-(2-aminothiazol-4-yl)-2-methoxyiminoacetamido]-2-carboxy-8-oxo-5-thia-1-azabicyclo[4.2.0]oct-2-ene (1.2 g) in the form of beige crystals.

Infra-red spectrum (KBr), characteristic bands (cm⁻¹): 3,330, 1,770, 1,710, 1,670, 1,625, 1,530, 1,360, 1,035.

Proton NMR spectrum (350 MHz, d₆-DMSO, δ in ppm J in Hz): 2.2 (s, 3H, CH₃CO—); 3.3 to 3.6 (m, 4H, —SCH₂— and —CH₂CO—); 4.0 (s, 3H, CH₃ON=); 5.10 (d, J=4, 1H, H₆); 5.82 (dd, J=4 and 9, 1H, H₇); 6.60 (s broad, 2H, —NH₂); 6.80 (s, 1H, H of the thiazole); 9.35 (d, J=9, 1H, —CONH—).

REFERENCE EXAMPLE 3

A solution of 2-benzhydryloxycarbonyl-7-t-butoxycarbonylamino-3-methyl-8-oxo-5-thia-1-azabicyclo[4.2.0]oct-2-ene (2.2 g) in hexamethylphosphorotriamide (7 cc) is added dropwise, in the course of 2 minutes, to a solution of 1-dimethylamino-1-methoxyethylene (1.85 g) in hexamethylphosphorotriamide (10 cc) at 80° C. The solution is stirred at 80° C. for 2 hours. The solution is gradually poured into a stirred mixture of distilled water (100 cc) and ethyl acetate (100 cc). The organic phase is separated off by decantation, washed with a 1N solution of citric acid (50 cc) and then with a saturated aqueous solution of sodum chloride (2×50 cc), dried over sodium sulphate and concentrated to dryness under reduced pressure (20 mm Hg; 2.7 kPa) at 20° C. The residue is chromatographed on a column of Merck silica gel (0.06–0.20) (50 g) (diameter of the column: 2 cm; height: 34 cm). Elution is carried out with a 25/75 (by volume) ethyl acetate/cyclohexane mixture, 50 cc fractions being collected. Fractions 4 to 9 are concentrated to dryness under reduced pressure (20 mm Hg; 2.7 kPa) at 30° C. This yields a mixture of 3-acetonyl-2-benzhydryloxycarbonyl-7-t-butoxycarbonylamino-8-oxo-5-thia-1-azabicyclo[4.2.0]oct-2-ene and -oct-3-ene (0.9 g) in the form of a hard, pale yellow foam.

Infra-red spectrum (CDCl$_3$), characteristic bands (cm$^{-1}$): 3,440, 1,780, 1,720, 1,505, 1,455, 1,395, 1,370, 1,160, 695.

Proton NMR spectrum (350 MHz, CDCl$_3$, δ in ppm, J in Hz); mixture of 65% of the oct-2-ene and 35% of the oct-3-ene: 1.45 (s, 9H, —C(CH$_3$)$_3$); 1.95 (s, —CO—CH$_3$ of the oct-3-ene); 2.09 (s, —CO—CH$_3$ of the oct-2-ene); 3.14 and 3.29 (2d, J=17, —CH$_2$—CO— of the oct-3-ene); 3.27 and 3.57 (2d, J=18, —S—CH$_2$— of the oct-2-ene); 3.56 and 3.68 (2d, J=17, —CH$_2$—CO— of the oct-2-ene); 5.01 (d, J=4, —H in the 6-position of the oct-2-ene); 5.10 (s, —H in the 2-position of the oct-3-ene); 5.21 (d, J=4, —H in the 6-position of the oct-3-ene); 5.25 (d, J=9, —CO—NH— of the oct-2-ene); 5.30 to 5.50 (m, —CO—NH— and —H in the 7-position of the oct-3-ene); 5.63 (dd, J=9 and 4, —H in the 7-position of the oct-2-ene); 6.09 (s, —H in the 4-position of the oct-3-ene); 6.81 (s, —COO—CH(C$_6$H$_5$)$_2$ of the oct-3-ene); 6.88 (s, —COO—C$\underline{H}$(C$_6$H$_5$)$_2$ of the oct-2-ene); 7.2 to 7.5 (m, aromatic protons).

A solution of 85% pure m-chloroperbenzoic acid (0.8 g) in methylene chloride (1.5 cc) is added, in the course of 10 minutes, to a solution of 3-acetonyl-2-benzhydryloxycarbonyl-7-t-butoxycarbonylamino-8-oxo-5-thia-1-azabicyclo[4.2.0]oct-2-ene and -oct-3-ene (0.2 g) in methylene chloride (1.5 cc) at −10° C. The solution is stirred for 15 minutes at 0° C. and then washed with a saturated aqueous solution of sodium bicarbonate (5 cc), dried over sodium sulphate and concentrated to dryness under reduced pressure (20 mm Hg; 2.7 kPa) at 20° C. The residue is chromatographed on a column of Merck silica gel (0.06-0.2) (2 g) (diameter of the column: 0.8 cm; height: 8 cm). Elution is carried out with a 50/50 (by volume) ethyl acetate/cyclohexane mixture (50 cc), 1 cc fractions being collected. Fractions 13 to 17 are concentrated to dryness under reduced pressure (20 mm Hg; 2.7 kPa) at 20° C. This yields 3-acetonyl-2-benzhydryloxycarbonyl-7-t-butoxycarbonylamino-8-oxo-5-thia-1-azabicyclo[4.2.0]oct-2-ene-5-oxide (50 mg) in the form of a pale yellow solid.

Proton NMR spectrum (350 MHz, d$_6$-DMSO, δ in ppm, J in Hz): 1.43 (s, 9H, —C(CH$_3$)$_3$); 2.00 (s, 3H, CH$_3$CO—); 3.53-3.68-3.80-3.83 (4d, J=19, 4H, —SCH$_2$— and —CH$_2$CO—); 4.98 (d, J=4, 1H, H$_6$); 5.75 (dd, J=4 and 10, 1H, H$_7$); 6.17 (d, J=10, 1H, —CONH—); 6.85 (s, 1H, —COOCH<).

REFERENCE EXAMPLE 4

A solution of p-toluenesulphonic acid monohydrate (3.8 g) in acetonitrile (50 cc) is added, in the course of 30 minutes, to a solution of 3-acetonyl-2-benzhydryloxycarbonyl-7-t-butoxycarbonylamino-8-oxo-5-thia-1-azabicyclo[4.2.0]oct-2-ene (5.23 g) in acetonitrile (50 cc) at 40° C. The mixture is kept at 40° C. for 30 minutes and then concentrated under reduced pressure (20 mm Hg; 2.7 kPa) at 40° C. to a volume of about 30 cc. It is diluted with methylene chloride (150 cc) and the solution is washed with a saturated aqueous solution of sodium bicarbonate (50 cc) and dried over magnesium sulphate. This yields a solution of 3-acetonyl-7-amino-2-benzhydryloxycarbonyl-8-oxo-5-thia-1-azabicyclo[4.2.0]oct-2-ene, which is identical to the product described in Reference Example 2.

The solution thus obtained is cooled to 4° C. and D-α-t-butoxycarbonylaminophenylacetic acid (2.51 g) and dicyclohexylcarbodiimide (2.27 g) are added. The mixture is stirred for 2 hours at 4° C. and then for 10 hours at 20° C. It is filtered and the filtrate is then concentrated to dryness under reduced pressure (20 mm Hg; 2.7 kPa) at 20° C. The residue is chromatographed on a column of Merck silica gel (0.06-0.2) (120 g) (diameter of the column: 3.5 cm; height: 28 cm). Elution is carried out with a 30/70 (by volume) ethyl acetate/cyclohexane mixture (1.5 liters), 100 cc fractions being collected. Fractions 5 to 10 are concentrated to dryness under reduced pressure (20 mm Hg; 2.7 kPa) at 20° C. This yields 3-acetonyl-2-benzhydryloxycarbonyl-7-D-α-t-butoxycarbonylaminophenylacetamido-8-oxo-5-thia-1-azabicyclo[4.2.0]oct-2-ene (2.2 g) in the form of a hard white foam.

Infra-red spectrum (CHCl$_3$), characteristic bands (cm$^{-1}$): 3,420, 1,780, 1,720, 1,695, 1,490, 1,450, 1,370, 1,160, 695.

Proton NMR spectrum (350 MHz, CDCl$_3$, δ in ppm, J in Hz): 1.46 (s, —C(CH$_3$)$_3$); 2.10 (s, —CO—CH$_3$); 3.18 and 3.46 (2d, J=18, —S—CH$_2$—); 3.58 (s, —CH$_2$—CO—); 4.95 (d, J=4, —H in the 6-position); 5.22 (m, >NH of the carbamate); 5.61 (d, J=7,

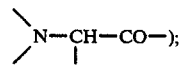

5.82 (dd, J=4 and 9, —H in the 7-position); 6.86 (s, —COO—CH(C$_6$H$_5$)$_2$); 7.2 to 7.5 (m, aromatic protons).

3-Acetonyl-2-benzhydryloxycarbonyl-D-α-7-t-butoxycarbonylaminophenylacetamido-8-oxo-5-thia-1-azabicyclo[4.2.0]oct-2-ene (2.2 g) is dissolved in a mixture of trifluoroacetic acid (50 cc) and anisole (4 cc). The solution is stirred at 20° C. for 20 minutes and then evaporated to dryness under reduced pressure (1 mm Hg; 0.13 kPa) at 20° C. Ethyl acetate (50 cc) is added and the mixture is concentrated to dryness under reduced pressure (20 mm Hg; 2.7 kPa) at 20° C. This operation is repeated 3 times. The residue is taken up in diisopropyl ether (100 cc). The insoluble material is filtered off and dried under pressure (1 mm Hg; 0.13 kPa) at 20° C. This yields 3-acetonyl-7-D-α-aminophenylacetamido-2-carboxy-8-oxo-5-thia-1-azabicyclo[4.2.0]oct-2-ene trifluoroacetate (2.0 g), which is dissolved in distilled water (200 cc). The solution is extracted with ethyl acetate (50 cc). The aqueous phase is treated with moist Amberlite IR-45 (OH$^\ominus$) resin (20 cc) until the pH has stabilised at approximately 5.25 (about 1 hour). The resin is filtered off. The aqueous phase is lyophilised. This yields 3-acetonyl-7-D-α-aminophenylacetamido-2-carboxy-8-oxo-5-thia-1-azabicyclo[4.2.0]oct-2-ene (0.46 g) in the form of a beige powder.

Infra-red spectrum (KBr), characteristic bands (cm$^{-1}$): 3,200, 3,100, 1,770, 1,690, 1,660, 1,570, 1,515, 1,500, 1,455, 750 and 700.

Proton NMR spectrum (350 MHz, CF$_3$COOD, δ in ppm, J in Hz): 2.28 (m, 3H, —CO—CH$_3$); 3.35 to 4 (m, 4H, —CH$_2$CO— and —S—CH$_2$—); 5.26 (d, J=4, 1H, —H in the 6-position); 5.55 (s, 1H,

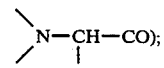

5.91 (d, J=4, 1H, —H in the 7-position); 7.5 to 7.8 (m, aromatic protons).

REFERENCE EXAMPLE 5

1-Dimethylamino-1-methoxyethylene (8.1 g) is added dropwise, in the course of 35 minutes, to a solution of 2-benzhydryloxycarbonyl-7-D-α-t-butoxycarbonylaminophenylacetamido-3-methyl-8-oxo-5-thia-1-azabicyclo[4.2.0]oct-2-ene (12.3 g) in dimethylformamide (80 cc) at 80° C., and the solution is then kept at 80° C. for 20 minutes. This yields a solution of 2-benzhydryloxycarbonyl-7-D-α-t-butoxycarbonylaminophenylacetamido-3-(2-dimethylaminoprop-1-en-1-yl)-8-oxo-5-thia-1-azabicyclo[4.2.0]oct-2-ene, which is poured into a stirred mixture of an N solution of citric acid (150 cc) and ethyl acetate (500 cc). The organic phase is decanted, dried over sodium sulphate and concentrated to dryness under reduced pressure (20 mm Hg; 2.7 kPa) at 20° C. This yields a mixture of 3-acetonyl-2-benzhydryloxycarbonyl-7-D-α-t-butoxycarbonylaminophenylacetamido-8-oxo-5-thia-1-azabicyclo[4.2.0]oct-2-ene and -oct-3-ene (11.5 g) in the form of a hard brown foam which is used without subsequent purification.

A solution of the mixture of 3-acetonyl-2-benzhydryloxycarbonyl-7-D-α-t-butoxycarbonylaminophenylacetamido-8-oxo-5-thia-1-azabicyclo[4.2.0]oct-2-ene and -oct-3-ene (17.4 g) in methylene chloride (300 cc) is cooled to 0° C. A solution of 85% pure m-chloroperbenzoic acid (5.4 g) in methylene chloride (150 cc) is added in the course of 40 minutes. The solution is stirred at 0° C. for 2 hours. The solution is washed with a saturated aqueous solution of sodium bicarbonate (50 cc) and then with distilled water (100 cc). The solution is dried over sodium sulphate and concentrated to dryness under reduced pressure (20 mm Hg; 2.7 kPa) at 20° C. The residue is chromatographed on a column of Merck silica gel (0.06–0.2) (250 g) (diameter of the column: 4.0 cm; height: 40 cm). Elution is carried out with a 65/35 (by volume) ethyl acetate/cyclohexane mixture (1.5 liters), 100 cc fractions being collected. Fractions 6 to 10 are concentrated to dryness under reduced pressure (20 mm Hg; 2.7 kPa) at 20° C. This yields 3-acetonyl-2-benzhydryloxycarbonyl-7-D-α-t-butoxycarbonylaminophenylacetamido-8-oxo-5-thia-1-azabicyclo[4.2.0]oct-2-ene-5-oxide (4.2 g) in the form of a beige powder.

Infra-red spectrum (KBr), characteristic bands (cm$^{-1}$): 3,340, 1,790, 1,715, 1,690, 1,660, 1,520, 1,495, 1,455, 1,390, 1,370, 1,170, 755, 740, 700.

Proton NMR spectrum (350 MHz, d$_6$-DMSO, δ in ppm, J in Hz): 1.42 (s, 9H, —C(CH$_3$)$_3$); 2.03 (s, 3H, —CH$_3$); 3.12 and 4.33 (2d, J=18, 2H, —SCH$_2$—); 3.26 (s broad, 2H, —CH$_2$CO—); 4.47 (d, J=4, 1H, H$_6$); 5.24 (broad, 1H, —NHCOO—); 5.87 (d, J=2, 1H,

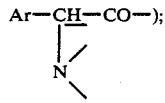

6.00 (dd, J=4 and 9, 1H, H$_7$); 6.83 (s, 1H, —COOCH<).

A solution of 3-acetonyl-2-benzhydryloxycarbonyl-7-D-α-t-butoxycarbonylaminophenylacetamido-8-oxo-5-thia-1-azabicyclo[4.2.0]oct-2-ene-5-oxide (0.67 g) in methylene chloride (10 cc) is cooled to −10° C. N,N-Dimethylacetamide (0.7 cc) and then phosphorus trichloride (0.18 cc) are added and the solution is stirred at −10° C. for 1 hour. The solution is then washed with a saturated aqueous solution of sodium bicarbonate (10 cc), dried over sodium sulphate and concentrated to dryness under reduced pressure (20 mm Hg; 2.7 kPa) at 20° C. This yields 3-acetonyl-2-benzhydryloxycarbonyl-7-D-α-t-butoxycarbonylaminophenylacetamido-8-oxo-5-thia-1-azabicyclo[4.2.0]oct-2-ene (0.50 g), the characteristics of which are identical to those of the product obtained in Reference Example 4.

REFERENCE EXAMPLE 6

A solution of 1-dimethylamino-1-methoxyethylene (1.62 g) in dimethylformamide (3 cc) is added, in the course of 45 minutes, to a solution of 2-benzhydryloxycarbonyl-3-methyl-7-phenoxyacetamido-8-oxo-5-thia-1-azabicyclo[4.2.0]oct-2-ene (2.06 g) in dimethylformamide (15 cc) at 80° C. The mixture is then stirred for 10 minutes at 80° C. This yields a solution of 2-benzhydryloxycarbonyl-7-phenoxyacetamido-3-(2-dimethylaminoprop-1-en-1-yl)-8-oxo-5-thia-1-azabicyclo[4.2.0]oct-2-ene, which is poured into a stirred mixture of ethyl acetate (100 cc), distilled water (50 cc) and 1N citric acid (50 cc) at 0° C. The organic phase is separated off by decantation, washed with distilled water (2×100 cc), dried over sodium sulphate and concentrated to dryness under reduced pressure (20 mm Hg; 2.7 kPa) at 30° C. The residue is chromatographed on a column of Merck silica gel (0.06–0.2) (20 g) (diameter of the column: 2 cm; height: 16 cm). Elution is carried out with a 28/72 (by volume) ethyl acetate/cyclohexane mixture (600 cc), 30 cc fractions being collected. Fractions 7 to 16 are concentrated to dryness under reduced pressure (20 mm Hg; 2.7 kPa) at 20° C. This yields 3-acetonyl-2-benzhydryloxycarbonyl-7-phenoxyacetamido-8-oxo-5-thia-1-azabicyclo[4.2.0]oct-2-ene (0.53 g) in the form of a hard yellow foam.

Infra-red spectrum (CHCl$_3$), characteristic bands (cm$^{-1}$): 3,420, 1,785, 1,725, 1,700, 1,660, 1,520, 1,495, 1,440, 690.

Proton NMR spectrum (80 MHz, CDCl$_3$, δ in ppm, J in Hz): 2.09 (s, 3H, —CO—CH$_3$); 3.10 to 3.90 (m, 4H, —CH$_2$—CO— and —S—CH$_2$—); 4.57 (s, 2H, —O—CH$_2$—CO—); 5.05 (d, J=5, 1H, —H in the 6-position); 6.93 (dd, J=9 and 5, 1H, —H in the 7-position); 6.95 (s and d, J=8, —COO—CH(C$_6$H$_5$)$_2$ and aromatic —H atoms in the ortho-position of the phenoxymethyl); 7.05 (t, J=8, aromatic —H in the para-position of the phenoxymethyl); 7.15 to 7.65 (m, aromatic protons and —CO—NH—).

A solution of 85% pure m-chloroperbenzoic acid (0.2 g) in methylene chloride (6 cc) is added, in the course of 25 minutes, to a solution of 3-acetonyl-2-benzhydryloxycarbonyl-7-phenoxyacetamido-8-oxo-5-thia-1-azabicyclo[4.2.0]oct-2-ene (0.56 g) in methylene chloride (12 cc), cooled to −10° C., and the mixture is then kept at −10° C. for 10 minutes. The solution is washed with a saturated aqueous solution of sodium bicarbonate (10 cc), dried over magnesium sulphate and then concentrated to dryness under reduced pressure (20 mm Hg; 2.7 kPa) at 20° C. The residue is chromatographed on a column of Merck silica gel (0.06–0.2) (10 g) (diameter of the column: 1.5 cm; height: 12 cm). Elution is carried out with a 50/50 (by volume) ethyl acetate/cyclohexane mixture (600 cc), 10 cc fractions being collected. Fractions 26 to 32 are concentrated to dryness under reduced pressure (20 mm Hg; 2.7 kPa) at 20° C. This yields 3-acetonyl-2-benzhydryloxycarbonyl-7-phenoxyacetamido-8-oxo-5-thia-1-azabicyclo[4.2.0]oct-2-ene-5-oxide (0.12 g) in the form of a white solid.

Proton NMR spectrum (360 MHz, DMSO, δ in ppm, J in Hz): 1.97 (s, 3H, —CH$_3$); 3.54 and 3.81 (2d, J=16, 2H, —CO—CH$_2$—); 3.70 and 3.87 (2d, J=18, 2H, —S(O)CH$_2$—); 4.72 (s, 2H, —OCH$_2$—); 5.04 (d, J=5, 1H, H$_6$); 6.12 (dd, J=5 and 9, 1H, H$_7$); 6.88 (s, 1H, —COOCH<); 8.16 (d, J=9, —CONH—).

REFERENCE EXAMPLE 7

A suspension consisting of a mixture of the E form of 2-benzhydryloxycarbonyl-7-t-butoxycarbonylamino-3-[α-(β-dimethylaminostyryl)]-8-oxo-5-thia-1-azabicyclo[4.2.0]oct-2-ene (0.21 g), ethyl acetate (5 cc) and 1N hydrochloric acid (3 cc) is stirred vigorously at 20° C. for 2 hours. The organic phase is decanted, washed with a saturated solution of sodium bicarbonate (3 cc) and then with water (2 cc), dried over magnesium sulphate and evaporated to dryness under reduced pressure (20 mm Hg; 2.7 kPa) at 20° C. This yields 2-benzhydryloxycarbonyl-7-t-butoxycarbonylamino-8-oxo-3-phenacyl-5-thia-1-azabicyclo[4.2.0]oct-2-ene (0.195 g) in the form of a hard, pale yellow foam.

Infra-red spectrum (CHBr$_3$), characteristic bands (cm$^{-1}$): 3,420, 1,785, 1,720, 1,690, 1,595, 1,580, 1,505, 1,495, 1,455, 1,450, 1,390, 1,370, 760, 745.

Proton NMR spectrum (350 MHz, CDCl$_3$, δ in ppm, J in Hz): 1.48 (s, 9H (CH$_3$)$_3$C—); 3.32 and 3.64 (2d, J=19, 2H, —CH$_2$S—); 4.09 and 4.47 (2d, J=17, 2H, —CH$_2$CO—); 5.04 (d, J=5, 1H, H in the 6-position); 5.31 (d, J=8, 1H, —CONH—); 5.64 (dd, J=5 and 8, 1H, H in the 7-position); 6.86 (s, 1H, —COOCH<).

A solution of this product (3 g) in acetonitrile (45 cc) is heated to 35° C., a solution of p-toluenesulphonic acid monohydrate (2.5 g) in acetonitrile (15 cc) is added all at once and the mixture is left for 2 hours at 35° C. The reaction mixture is then poured into a saturated solution of sodium bicarbonate (50 cc) and extracted with ethyl acetate (150 cc), and the organic phase is washed with water (2×100 cc), dried over magnesium sulphate and evaporated to dryness under reduced pressure (20 mm Hg; 2.7 kPa) at 20° C. This yields 7-amino-2-benzhydryloxycarbonyl-8-oxo-3-phenacyl-5-thia-1-azabicyclo[4.2.0]oct-2-ene (1.9 g) in the form of a hard brown foam.

Infra-red spectrum (CHCl$_3$), characteristic bands (cm$^{-1}$): 3,520, 3,440, 1,780, 1,725, 1,675, 1,620, 1,600, 1,580, 1,495, 1,450, 695.

Proton NMR spectrum (350 MHz, CDCl$_3$, δ in ppm, J in Hz): 3.28 and 3.63 (2d, J=18, 2H, —CH$_2$S—); 4.00 and 4.42 (2d, J=17, 2H, —CH$_2$CO—); 4.70 and 4.99 (2d, J=4, 2H, H$_6$ and H$_7$); 6.88 (s, 1H, —COOCH<).

REFERENCE EXAMPLE 8

A solution of tris-dimethylaminomethylbenzene (7 g) in dioxane (50 cc) is added, in the course of 8 minutes, to a solution of 2-benzhydryloxycarbonyl-7-t-butoxycarbonylamino-3-methyl-8-oxo-5-thia-1-azabicyclo[4.2.0]oct-2-ene (7.6 g) in dioxane (50 cc) at 80° C., and the mixture is kept at 80° C. for 12 minutes, whilst stirring. At this stage, a mixture of the Z and E forms of 2-benzhydryloxycarbonyl-7-t-butoxycarbonylamino-3-[α-(β-dimethylaminostyryl)]-8-oxo-5-thia-1-azabicyclo[4.2.0]oct-2-ene and -oct-3-ene is obtained. The reaction mixture is poured into a stirred mixture of ethyl acetate (200 cc), 1N hydrochloric acid (20 cc) and ice (20 g). The stirring is continued at 20° C. for 22 hours. The organic phase is separated off, washed with a saturated solution of sodium bicarbonate (50 cc) and then with distilled water (2×100 cc), dried over magnesium sulphate and evaporated to dryness under reduced pressure (20 mm Hg; 2.7 kPa) at 20° C. The residue (11.2 g) is dissolved in a 30/70 (by volume) ethyl acetate/cyclohexane mixture (100 cc). The solution is then filtered on Merck silica gel (0.06–0.2) (50 g) and washed through with the same mixture (200 cc) and the filtrate is evaporated. This yields a mixture of 2-benzhydryloxycarbonyl-7-t-butoxycarbonylamino-8-oxo-3-phenacyl-5-thia-1-azabicyclo[4.2.0]oct-2-ene and -oct-3-ene (8.3 g) in the form of a hard blond foam.

Infra-red spectrum (CHBr$_3$), characteristic bands (cm$^{-1}$): 3,420, 1,785, 1,720, 1,690, 1,595, 1,580, 1,505, 1,495, 1,455, 1,450, 1,390, 1,370, 760, 745.

Proton NMR spectrum (350 MHz, CDCl$_3$, δ in ppm, J in Hz); 50/50 mixture of oct-2-ene and oct-3-ene: 1.45 (s, 9H, —C(CH$_3$)$_3$ of the oct-2-ene and oct-3-ene); 3.32 and 3.67 (2d, J=18, 1H, —SCH$_2$— of the oct-2-ene); 3.69 and 3.92 (2d, J=17, 1H, —CH$_2$CO— of the oct-3-ene); 4.08 and 4.46 (2d, J=17, 1H, —CH$_2$CO— of the oct-2-ene); 5.07 (d, J=5, 0.5H, H in the 6-position of the oct-2-ene); 5.24 (d, J=4, 0.5H, H in the 6-position of the oct-3-ene); 5.30 (s, 0.5H, H in the 2-position of the oct-3-ene); 5.20 to 5.35 (m, 0.5H, —CONH— of the oct-2-ene); 5.35 to 5.50 (m, 1H, H in the 7-position and —CONH— of the oct-3-ene); 5.64(d,d, J=5 and 9, 0.5H, —H in the 7-position of the oct-2-ene); 6.14 (s, 0.5H, H in the 4-position of the oct-3-ene); 6.86 (s, 1H, —COOCH< of the oct-2-ene and oct-3-ene).

85% pure m-chloroperbenzoic acid (1.6 g) is added to a solution of a mixture of 2-benzhydryloxycarbonyl-7-t-butoxycarbonylamino-8-oxo-3-phenacyl-5-thia-1-azabicyclo[4.2.0]oct-2-ene and -oct-3-ene (4.5 g) in methylene chloride (90 cc) at 5° C., and the mixture is left for 30 minutes at 5° C., whilst stirring. The reaction mixture is poured into a saturated solution of sodium bicarbonate (50 cc); the organic phase is washed with distilled water (50 cc), dried over magnesium sulphate and evaporated to dryness under reduced pressure (20 mm Hg; 2.7 kPa) at 20° C. The residue (4.25 g) is fixed onto Merck silica gel (0.06–0.2) (20 g) and chromatographed on a column of Merck silica gel (0.06–0.2) (150 g) (diameter of the column: 3.6 cm; height: 40 cm). Elution is carried out first with an 80/20 (volume) ethyl acetate/cyclohexane mixture (700 cc), then with a 70/30 (by volume) ethyl acetate/cyclohexane mixture (1 liter), a 65/35 mixture (500 cc) and a 60/40 mixture (500 cc), and finally with a 50/50 mixture (1 liter), 50 cc fractions being collected. Fractions 47 to 56 are combined and the solvent is evaporated off to dryness under reduced pressure (20 mm Hg; 2.7 kPa) at 20° C. This yields 2-benzhydryloxycarbonyl-7-t-butoxycarbonylamino-8-oxo-3-phenacyl-5-thia-1-azabicyclo[4.2.0]oct-2-ene-5-oxide (2.5 g) in the form of a hard brown foam.

Infra-red spectrum (CHCl$_3$), characteristic bands (cm$^{-1}$): 3,410, 1,800, 1,715, 1,685, 1,595, 1,580, 1,500, 1,445, 1,390, 1,370, 1,165, 1,040.

Proton NMR spectrum (350 MHz, CDCl$_3$, δ in ppm, J in Hz): 1.50 (s, 9H, (CH$_3$)$_3$C—); 3.62 (s, 2H, —CH$_2$CO—); 3.65 and 5.28 (2d, J=18, 2H, —CH$_2$S→O); 4.65 (d, J=4, 1H, H in the 6-position); 5.82 (s broad, 2H, H in the 7-position and —CONH—); 6.86 (s, 1H, —COOCH<).

2-Benzhydryloxycarbonyl-7-t-butoxycarbonylamino-8-oxo-3-phenacyl-5-thia-1-azabicyclo[4.2.0]oct-2-ene-5-oxide (10.1 g) is added to a solution of p-toluenesulphonic acid monohydrate (8.15 g) in acetonitrile (170 cc), warmed to 35° C., and the mixture is left at 35° C. for 1 hour, whilst stirring. The reaction mixture is then poured into a stirred mixture of a saturated solution of sodium bicarbonate (150 cc) and ethyl acetate (300 cc). The organic phase is then washed with distilled water (100 cc), dried over magnesium sulphate and evaporated to dryness under reduced pressure (20 mm Hg; 2.7 kPa) at 20° C. This yields crude 7-amino-2-benzhydryloxycarbonyl-8-oxo-3-phenacyl-5-thia-1-azabicyclo[4.2.0]oct-2-ene-5-oxide (7 g) in the form of a thick oil which can be used without purification.

A solution of dicyclohexylcarbodiimide (1.08 g) in methylene chloride (10 cc) is added, whilst stirring, to a solution of 7-amino-2-benzhydryloxycarbonyl-8-oxo-3-phenacyl-5-thia-1-azabicyclo[4.2.0]oct-2-ene-5-oxide (2.37 g), D-α-t-butoxycarbonylaminophenylacetic acid (1.32 g) and 4-dimethylaminopyridine (0.01 g) in methylene chloride (25 cc) at 20° C., and the mixture is stirred for 2 hours at 20° C. The reaction mixture is filtered and the filtrate is evaporated to dryness under reduced pressure (20 mm Hg; 2.7 kPa) at 20° C. The residue is dissolved in ethyl acetate (60 cc), the solution is washed with a saturated solution of sodium bicarbonate (30 cc) and then with distilled water (25 cc) and dried over magnesium sulphate and the solvent is evaporated off to dryness under reduced pressure (20 mm Hg; 2.7 kPa) at 20° C. This yields a solid (3.6 g) which is suspended in isopropyl ether (50 cc). After filtering the suspension, drying the solution over sodium sulphate and evaporating off the solvent, 2-benzhydryloxycarbonyl-7-(D-α-t-butoxycarbonylaminophenylacetamido)-8-oxo-3-phenacyl-5-thia-1-azabicyclo[4.2.0]oct-2-ene-5-oxide (2.45 g) is obtained in the form of a light brown powder.

Infra-red spectrum (CHCl$_3$), characteristic bands (cm$^{-1}$): 3,420, 3,380, 1,800, 1,710, 1,690, 1,595, 1,585, 1,575, 1,510, 1,490, 1,480, 1,450, 1,445, 1,390, 1,365, 1,165, 1,045.

Proton NMR spectrum (350 MHz, CDCl$_3$, δ in ppm, J in Hz): 3.52 (s, 2H, —CH$_2$CO—); 3.63 and 5.21 (2d, J=18, 2H, —CH$_2$S→O); 4.58 (d, J=4, H in the 6-position); 5.56 and 5.80 (2s broad, 2H, —CH(NH—)CO); 6.06 (dd, J=4 and 7, 1H, H in the 7-position); 6.83 (s, 1H, —COOCH<).

Phosphorus trichloride (0.71 cc) is added to a solution of 2-benzhydryloxycarbonyl-7-(D-α-t-butoxycarbonylaminophenylacetamido)-8-oxo-3-phenacyl-5-thia-1-azabicyclo[4.2.0]oct-2-ene-5-oxide (3 g) in methylene chloride (30 cc) and dimethylacetamide (1.65 cc), cooled to −7° C., and the reaction mixture is stirred at −3° C. for 45 minutes. The mixture is then poured into ethyl acetate (100 cc), washed with a saturated solution of sodium bicarbonate (30 cc) and water (2×30 cc), dried over magnesium sulphate and filtered and the filtrate is concentrated to dryness under reduced pressure (20 mm Hg; 2.7 kPa) at 20° C. The residue (3.2 g) is dissolved in a 25/75 (by volume) ethyl acetate/cyclohexane mixture (30 cc) and is chromatographed on a column of Merck silica gel (0.04–0.06) (200 g) (diameter of the column: 3.6 cm; height: 39 cm). Elution is carried out with a 25/75 (by volume) ethyl acetate/cyclohexane mixture (1.5 liters) under a pressure of 40 kPa, 50 cc fractions being collected. Fractions 21 to 29 are collected and evaporated to dryness under reduced pressure (20 mm Hg; 2.7 kPa) at 20° C. 2-Benzhydryloxycarbonyl-7-(D-α-t-butoxycarbonylaminophenylacetamido)-8-oxo-3-phenacyl-5-thia-1-azabicyclo[4.2.0]oct-2-ene (1 g) is collected in the form of a hard yellow foam.

Infra-red spectrum (CHCl$_3$), characteristic bands (cm$^{-1}$): 3,420, 1,790, 1,720, 1,690, 1,595, 1,580, 1,495, 1,455, 1,450, 1,390, 1,370, 1,160.

Proton NMR spectrum (350 MHz, CDCl$_3$, δ in ppm, J in Hz): 1.44 (s, 9H, (CH$_3$)$_3$C—); 3.21 and 3.53 (2d, J=18, 2H, —SCH$_2$—); 4.09 and 4.34 (2d, J=18, 2H, —CH$_2$CO—); 5.00 (d, J=4, 1H, H in the 6-position); 5.22 (m broad, —NH— of the carbamate); 5.64 (d, J=7, 1H,

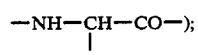

5.83 (dd, J=4 and 7, 1H, H in the 7-position); 6.58 (s broad, 1H, —CONH— of the amide); 6.85 (s, 1H, —COOCH<).

2-Benzhydryloxycarbonyl-7-(D-α-t-butoxycarbonylaminophenylacetamido)-8-oxo-3-phenacyl-5-thia-1-azabicyclo[4.2.0]oct-2-ene (1 g) is dissolved in trifluoroacetic acid (13.9 cc) and the mixture is stirred for 20 minutes at 20° C. The trifluoroacetic acid is evaporated off under reduced pressure (1 mm Hg; 0.13 kPa). The residue is taken up in ethyl acetate (2×20 cc), each solution being concentrated to dryness under reduced pressure (20 mm Hg; 2.7 kPa), in order to drive off the maximum amount of trifluoroacetic acid; the final residue is dissolved in ethyl acetate (5 cc) and the solution thus obtained is added dropwise to isopropyl ether (30 cc), whilst stirring vigorously. The precipitate obtained is filtered off, washed with isopropyl ether (5 cc) and dried in vacuo (1 mm Hg. 0.13 kPa). This yields 7-(D-α-aminophenylacetamido)-2-carboxy-8-oxo-3-phenacyl-5-thia-1-azabicyclo[4.2.0]oct-2-ene trifluoroacetate (0.72 g) in the form of a whitish powder.

Infra-red spectrum (KBr), characteristic bands (cm$^{-1}$): 3,300–2,150, 1,770, 1,680, 1,600, 1,580, 1,520, 1,495, 1,450, 1,200, 1,130, 800, 755, 720, 700.

Proton NMR spectrum (350 MHz, CF$_3$COOD, δ in ppm, J in Hz): 3.49 and 3.72 (2d, J=18, 2H, —SCH$_2$—); 4.48 and 4.69 (2d, J=17, 2H, —CH$_2$CO—); 5.31 (d, J=4, 1H, H in the 6-position); 5.91 (d, J=4, 1H, H in the 7-position); 5.51 (s broad, 1H, —CH(N<)CO—); 7.50 to 8.03 (m, 10H, aromatic protons).

REFERENCE EXAMPLE 9

A solution of 7-amino-2-benzhydryloxycarbonyl-8-oxo-3-phenacyl-5-thia-1-azabicyclo[4.2.0]oct-2-ene-5-oxide (1.25 g) and triethylamine (1.05 cc) in methylene chloride (10 cc), cooled to 0° C., is added, in the course of 1 minute, to a solution of 2-methoxy-2-(2-tritylaminothiazol-4-yl)-acetyl chloride (prepared from 2-methoxyimino-2-(2-tritylaminothiazol-4-yl)-acetic acid (1.21 g), a 2.4M solution of phosgene in chlorobenzene (1.3 cc) and dimethylacetamide (0.23 cc) in methylene chloride (15 cc) over a period of 16 hours at −7° C.) at −10° C. The reaction mixture is stirred for 1 hour at −5° C. and then for 1 hour whilst allowing the temperature to rise from −5° C. to 20° C., and is then poured into 0.5N hydrochloric acid (5 cc). The organic phase is washed with water (10 cc), dried over magnesium sulphate and evaporated to dryness under reduced pressure (20 mm Hg; 2.7 kPa) at 20° C. The residue is solidified in isopropyl ether (20 cc). In this way, the syn isomer of 2-benzyhydryloxycarbonyl-7-[2-methoxyimino-2-(2-tritylaminothiazol-4-yl)-acetamido]-8-oxo-3-phenacyl-5-thia-1-azabicyclo[4.2.0]oct-2-ene-5-oxide (2 g) is obtained in the form of an orange solid.

Infra-red spectrum (CHCl₃), characteristic bands (cm⁻¹): 3,400, 1,800, 1,725, 1,680, 1,590, 1,580, 1,510, 1,490, 1,445, 1,040, 690.

Proton NMR spectrum (350 MHz, CDCl₃, δ in ppm, J in Hz): [3.59 (s broad, 2H) and 3.68 and 5.22 (2d, J=18, 2H), —CH₂S— and —CH₂CO—]; 4.09 (s, 3H, =NOCH₃); 4.71 (d, J=5, 1H, H in the 6-position); 6.16 (dd, J=5 and 9, 1H, H in the 7-position); 6.74 (s, 1H, H of the thiazole); 6.85 (s, 1H, —COOCH<); 7.07 (s broad, 1H, —NHC(C₆H₅)₃); 7.50 (d, J=9, 1H, —CONH—).

Phosphorus trichloride (0.81 cc) is added, in the course of 1 minute, to a solution of the syn isomer of 2-benzhydryloxycarbonyl-7-[2-methoxyimino-2-(2-tritylaminothiazol-4-yl)-acetamido]-8-oxo-3-phenacyl-5-thia-1-azabicyclo[4.2.0]oct-2-ene-5-oxide (4.3 g) and dimethylacetamide (1.88 cc) in methylene chloride (43 cc), cooled to −8° C., and the mixture is left for 1 hour at −8° C., whilst stirring. The mixture is then poured into a saturated solution of sodium bicarbonate (20 cc) and ethyl acetate (100 cc). The organic phase is washed with water (30 cc), dried over magnesium sulphate and evaporated to dryness under reduced pressure (20 mm Hg; 2.7 kPa) at 20° C. The residue is dissolved in ethyl acetate (15 cc) and the solution is filtered on Merck silica gel (0.06–0.2) (13 g) and washed through with ethyl acetate (20 cc). The filtrate is evaporated to dryness under reduced pressure (20 mm Hg; 2.7 kPa) at 20° C. This yields the syn isomer of 2-benzhydryloxycarbonyl-7-[2-methoxyimino-2-(2-tritylaminothiazol-4-yl)-acetamido]-8-oxo-3-phenacyl-5-thia-1-azabicyclo[4.2.-0]oct-2-ene (3.6 g) in the form of a beige solid.

Infra-red spectrum (CHCl₃), characteristic bands (cm⁻¹): 3,400, 2,820, 1,780, 1,725, 1,680, 1,590, 1,580, 1,520, 1,490, 1,450, 1,040.

Proton NMR spectrum (350 MHz, CDCl₃, δ in ppm, J in Hz): 3.30 and 3.63 (2d, J=18, 2H, —CH₂S—); 4.07 (s, 3H, =NOCH₃); 4.11 and 4.40 (2d, J=18, 2H, —CH₂CO—); 5.11 (d, J=5, 1H, H in the 6-position); 5.95 (dd, J=5 and 9, 1H, H in the 7-position); 6.77 (s, 1H, H of the thiazole); 6.87 (s, 1H, —COOCH<); 6.91 (d, J=9, 1H, —CONH—); 7.03 (s, 1H, —N,HC(C₆H₅)₃).

The syn isomer of 2-benzhydryloxycarbonyl-7-[2-methoxyimino-2-(2-tritylaminothiazol-4yl)-acetamido]-8-oxo-3-phenacyl-5-thia-1-azabicyclo[4.2.0]oct-2-ene (2.7 g) is dissolved in formic acid (55 cc) at 20° C. Distilled water (11 cc) is added and the mixture is heated for 15 minutes at 45° C. The mixture is cooled to 20° C., diluted with water (44 cc) and filtered. The filtrate is concentrated to dryness under reduced pressure (5 mm Hg; 0.67 kPa) at 20° C. The residue is taken up in ethanol (3×50 cc), the solvent being evaporated off each time under reduced pressure (5 mm Hg; 0.67 kPa) at 20° C. in order to remove the water and the formic acid. The final residue is taken up in a saturated solution of sodium bicarbonate (50 cc) and the aqueous phase is washed with ethyl acetate (50 cc) and acidified to pH 3 with 1N hydrochloric acid, whilst stirring, in the presence of ethyl acetate (100 cc). The organic phase is dried over magnesium sulphate and evaporated to dryness under reduced pressure (20 mm Hg; 2.7 kPa) at 20° C. This yields the syn isomer of 7-[2-(2-aminothiazol-4-yl)-2-methoxyiminoacetamido]-2-carboxy-8-oxo-3-phenacyl-5-thia-1-azabicyclo[4.2.0]oct-2-ene (0.54 g) in the form of a beige solid.

Infra-red spectrum (KBr), characteristic bands (cm⁻¹): 3,340, 3,250 to 2,200, 1,770, 1,675, 1,630, 1,595, 1,580, 1,530, 1,445, 1,040, 690.

Proton NMR spectrum (350 MHz, d₆-DMSO, δ in ppm J in Hz): 3.45 and 3.63 (2d, J=18, 2H, —CH₂S—); 3.85 (s, 3H, =N—OCH₃); 4.20 and 4.45 (2d, J=18, 2H, —CH₂CO—); 5.17 (d, J=5, 1H, H in the 6-position); 5.75 (dd, J=5 and 9, 1H, H in the 7-position); 6.75 (s, 1H, H of the thiazole); 7.2 (s, 2H, —NH₂); 9.65 (d, J=9, 1H, —CONH—).

The syn isomer of 7-[2-(2-aminothiazol-4-yl)-2-methoxyiminoacetamido]-2-carboxy-8-oxo-3-phenacyl-5-thia-1-azabicyclo[4.2.0]oct-2-ene can be used by analogy with the method described in Reference Example 1 for preparing a product of the general formula (XVII).

We claim:

1. A cephalosporin derivative of the formula:

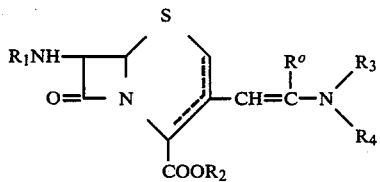

which is in the form of a bicyclooct-2-ene or bicyclooct-3-ene, in which formula the symbols R₃ and R₄, which are identical or different, represent alkyl (unsubstituted or substituted by alkoxy or dialkylamino) or phenyl, or together form, with the nitrogen atom to which they are attached, a 5- or 6-membered saturated heterocyclic ring or a said ring having another hetero-atom chosen from nitrogen, oxygen and sulphur, and unsubstituted or substituted by alkyl, (a) the symbol R₁ represents a radical of the formula:

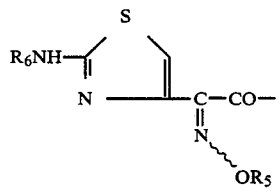

[[in which R₅ is hydrogen, alkyl, vinyl or cyanomethyl, an oxime-protecting group chosen from trityl, tetrahydropyranyl and 2-methoxy-prop-2-yl or a radical of the formula:

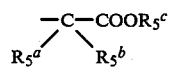

(in which Rᵃ₅ and Rᵇ₅, which are identical or different, are hydrogen or alkyl, or together form an alkylene having 2 or 3 carbon atoms, and Rᶜ₅ is an acid-protecting radical chosen from methoxymethyl, t-butyl, benzhydryl, benzyl, nitrobenzyl or p-methoxybenzyl) and R₆ is an amino-protecting radical chosen from t-butoxycarbonyl, trityl, benzyl, dibenzyl, benzyloxycarbonyl, p-nitrobenzyloxycarbonyl, p-methoxybenzyloxycarbonyl or a radical of the formula:

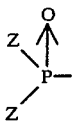

in which the symbols Z represent phenyl or radicals —OZ′, in which Z′ represents an alkyl, 2,2,2-trichloroethyl, phenyl or benzyl (it being possible for the said phenyl or benzyl to be substituted by an alkyl, alkoxy or nitro), or alternatively the symbols Z′ of the two substituents Z together form an alkylene having 2 or 3 carbon atoms]], benzhydryl or trityl, an acyl radical of the formula:

$R_7CO—$

[in which $R_7$ is alkyl substituted by phenyl or phenoxy]], a radical of the formula:

$R_8OCO—$

[[in which $R_8$ is an unsubstituted branched alkyl or a linear or branched alkyl carrying one or more substituents [chosen from amongst phenyl and phenyl substituted by alkoxy, nitro or phenyl] or vinyl, or a radical $Z_2P(O)$— as hereinbefore defined, or alternatively $R_1NH$ is replaced by methyleneamino in which the methylene is substituted by a dialkylamino or aryl group (which is itself unsubstituted or substituted by one or more methoxy or nitro groups), the symbol $R_2$ represents an acid-protecting radical chosen from methoxymethyl, t-butyl, benzhydryl, benzyl, nitrobenzyl or p-methoxybenzyl and the symbol R° represents a radical of a first group consisting of a phenyl unsubstituted or substituted by an alkyl, trifluoromethyl, dialkylaminomethyl, alkoxy, alkylthio or dialkylamino or by a halogen atom selected from fluorine or chlorine, or a 5- or 6-membered heterocyclic radical having a single hetero-atom, selected from pyrid-2-yl or pyrid-3-yl, thien-2-yl or thien-3-yl or furan-2-yl or furan-3-yl, and which is unsubstituted or substituted by alkyl, alkoxy or dimethylaminomethyl, or a radical of a second group designated as a radical —$CHR_9R_{10}$ consisting of an alkyl having 1 to 5 carbon atoms, benzyl substituted or substituted by a halogen atom or an alkyl, alkoxy, alkylthio, dialkylamino or trifluoromethyl, a methyl substituted by a 5- or 6-membered aromatic heterocyclic ring selected from pyrid-2-yl or pyrid-3-yl, thien-2-yl or thien-3-yl or furan-2-yl or furan-3-yl, a cycloalkyl having 3 to 6 ring members, or a radical —$CHR_9R_{10}$ in which $R_9$ and $R_{10}$, together with the carbon atom to which they are attached, form a 5- or 6-membered heterocyclic ring having an oxygen or sulphur atom, or alternatively (b) the symbol $R_1$ represents trityl or silyl, alkoxycarbonyl, the alkyl part of which has 1 to 5 carbon atoms, and which is unsubstituted or substituted by one or more phenyls or furyls, 2-(biphenyl-4-yl)-propoxycarbonyl, or a radical of the formula:

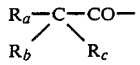

in which $R_a$ is an unsubstituted or substituted phenyl, thienyl, furyl, cyclohexadienyl or cyclohexenyl, $R_b$ is a hydrogen atom and $R_c$ is a hydrogen atom, an optionally protected hydroxyl, a protected amino or an optionally protected sulpho, or $R_a$ is an unsubstituted or substituted phenoxy or a pyridylthio and $R_b$ and $R_c$ are hydrogen atoms, or alternatively $R_a$ is phenyl, thienyl or furyl and $R_b$ and $R_c$ together form an alkoxyimino, cycloalkoxyimino or phenylalkoxyimino in the syn form, the symbol $R_2$ represents an acid-protective radical chosen from a phenyl group polysubstituted by aliphatic or aromatic radicals, an aromatic heterocyclic group having an oxygen or sulphur ring member, a t-alkyl, unsubstituted or substituted diphenylmethyl, alkoxyphenylalkyl, dimethoxybenzyl, nitrobenzyl, 4,5-dimethoxy-2-nitrobenzyl or furfuryl group, or a 2-oxa(or 2-thia)-cycloalkyl or 2-oxa(or 2-thia)-cycloalkenyl group having 5 to 7 ring members, or a nitrophenyl or 2,4-dinitrophenyl group, or silyl substituted by alkoxy, cycloalkyl, phenyl or phenylalkyl, and the symbol R° represents an alkyl (having 1 to 7 carbon atoms), a cycloalkyl (having 3 to 7 carbon atoms), a cycloalkyl-alkyl (having 4 to 7 carbon atoms), a phenyl or naphthyl radical, a phenylalkyl radical or a 5- or 6-membered heterocyclic radical having 1 to 4 hetero-atoms chosen from amongst nitrogen, oxygen or sulphur, or 5- or 6-membered heterocyclylalkyl radical in which the heterocyclic moiety has 1 to 4 heteroatoms chosen from amongst nitrogen, oxygen or sulphur, it being possible for these radicals R° to be unsubstituted or substituted by alkyl or alkoxy, and it being understood that (unless otherwise mentioned) the alkyl or acyl portions or radicals are linear or branched and have 1 to 4 carbon atoms.

2. A cephalosporin derivative according to claim 1, as defined under (a), in which $R_1$ represents a radical of the formula:

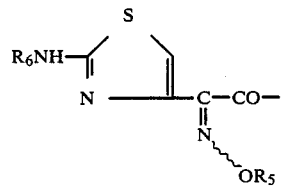

in which $R_5$ is hydrogen, alkyl, vinyl, cyanomethyl, trityl, tetrahydropyranyl or 2-methoxyprop-2-yl or a radical of the formula:

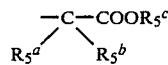

in which $R^a_5$ and $R^b_5$ are defined as in claim 1 and $R^c_5$ is methoxymethyl, t-butyl, benzhydryl, benzyl, nitrobenzyl or p-methoxybenzyl.

3. A cephalosporin derivative according to claim 1, as defined under (a), in which $R_1$ represents a radical

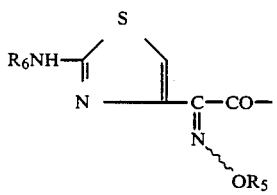

in which R₆ is chosen from amongst t-butoxycarbonyl, trityl, benzyl, dibenzyl, benzyloxycarbonyl, p-nitrobenzyloxycarbonyl, p-methoxybenzyloxycarbonyl or a radical Z₂P(O)— as defined in claim 1.

4. A cephalosporin derivative according to claim 1, as defined under (a), in which R₂ is chosen from amongst methoxymethyl, t-butyl, benzhydryl, benzyl, nitrobenzyl or p-methoxybenzyl.

5. A cephalosporin derivative according to claim 1, as defined under (b), in which R₂ is a phenyl group polysubstituted by aliphatic or aromatic radicals, an aromatic heterocyclic group having an oxygen or sulphur ring member, a t-alkyl, unsubstituted or substituted diphenylmethyl, alkoxyphenylalkyl, dimethoxybenzyl, nitrobenzyl, 4,5-dimethoxy-2-nitrobenzyl or furfuryl group, or a 2-oxa(or 2-thia)-cycloalkyl or 2-oxa(or 2-thia)-cycloalkenyl group having 5 to 7 ring members, or a nitrophenyl or 2,4-dinitrophenyl groups, or silyl substituted by alkoxy, cycloalkyl, phenyl or phenylalkyl.

6. A cephalosporin derivative according to claim 1, as defined under (b), in which R₁ represents a radical of the formula:

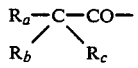

in which, $R_a$, $R_b$ and $R_c$ being defined according to claim 1, the phenyl and phenoxy radicals represented by $R_a$ can be substituted by hydroxyl, alkoxy, alkanoyloxy, benzoyloxy, 4-carbamoyloxy, protected amino or alkylamino, dialkylamino, alkylsulphonylamino, aminomethyl or t-butoxycarbonylaminomethyl groups or by a halogen atom, and the thienyl, furyl, cyclohexadienyl and cyclohexenyl radicals represented by $R_a$ can be substituted by protected aminomethyl radicals in the 5-position on the thienyl and furyl radicals and in the 2- or 3-position on the cyclohexadienyl and cyclohexenyl radicals.

7. A cephalosporin derivative according to claim 1, in which the symbol R₁ is trityl, a radical of the formula

in which R₇ is defined as in claim 1, a radical of the formula

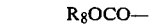

in which R₈ is defined as in claim 1, or a radical of the formula

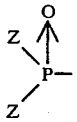

in which Z is defined as in claim 1, and the symbol R₂ represents a protective radical such as defined under (a) in claim 1, or alternatively the symbol R₁ represents a radical of the formula

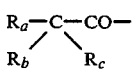

in which $R_a$, $R_b$ and $R_c$ are defined as in claim 1, and the symbol R₂ is a protective radical as defined under (b) in claim 1, the symbol R° is an alkyl or phenyl and the symbols R₃ and R₄ represent alkyl.

8. A cephalosporin derivative according to claim 1, in which the symbol R₁ represents trityl, phenoxyacetyl, a radical of the general formula R₈OCO— in which R₈ is a branched alkyl radical, a radical of the general formula (Z)₂P(O)— in which Z is an alkoxy radical, or an α-amino-α-phenylacetamido radical, the amine group of which is protected, the symbol R₂ is benzhydryl or nitrobenzyl, the symbol R° is methyl or phenyl and the symbols R₃ and R₄ are methyl.

9. 2-Benzhydryloxycarbonyl-7-t-butoxycarbonylamino-3-(2-dimethyl-aminoprop-1-en-1-yl)-8-oxo-5-thia-1-azabicyclo[4.2.0]oct-2-ene.

10. 2-Benzhydryloxycarbonyl-7-t-butoxycarbonylamino-3-[α-(β-dimethylaminostyryl)]-8-oxo-5-thia-1-azabicyclo-[4.2.0]oct-2-ene.

11. 7-t-Butoxycarbonylamino-3-(2-dimethylaminoprop-1-en-1-yl)-2-(4-methoxybenzyloxycarbonyl)-8-oxo-5-thia-1-azabicyclo-[4.2.0]oct-2-ene.

12. 2-Benzhydryloxy-carbonyl-3-(2-dimethylaminoprop-1-en-1-yl)-8-oxo-7-trityl-amino-5-thia-1-azabicyclo[4.2.0]oct-2-ene and -oct-3-ene.

13. 2-Benzhydryloxycarbonyl-7-diethoxyphosphoramido-3-(2-dimethylaminoprop-1-en-1-yl)-8-oxo-5-thia-1-azabicyclo[4.2.0]oct-2-ene.

* * * * *